(12) United States Patent
Obeid et al.

(10) Patent No.: US 11,141,429 B2
(45) Date of Patent: Oct. 12, 2021

(54) COMPOSITION AND USE OF MACRO-MINERALS TO LOWER POSTPRANDIAL GLYCEMIC RESPONSE AND REDUCE BODY WEIGHT

(71) Applicant: American University of Beirut, Beirut (LB)

(72) Inventors: Omar Obeid, Beirut (LB); Imad Toufeili, Beirut (LB); Ammar Olabi, Beirut (LB); Sani Hlais, Beirut (LB)

(73) Assignee: American University of Beirut, Beirut (LB)

( * ) Notice: Subject to any disclaimer, the term of this patent is extended or adjusted under 35 U.S.C. 154(b) by 0 days.

(21) Appl. No.: 16/668,657

(22) Filed: Oct. 30, 2019

(65) Prior Publication Data

US 2020/0061111 A1 Feb. 27, 2020

Related U.S. Application Data

(62) Division of application No. 15/459,412, filed on Mar. 15, 2017, now abandoned.

(60) Provisional application No. 62/308,546, filed on Mar. 15, 2016.

(51) Int. Cl.

| | | |
|---|---|---|
| *A61K 33/42* | (2006.01) |
| *A61K 33/06* | (2006.01) |
| *A61K 33/00* | (2006.01) |
| *A21D 2/18* | (2006.01) |
| *A23L 33/125* | (2016.01) |
| *A21D 2/02* | (2006.01) |
| *A21D 13/062* | (2017.01) |
| *A23L 33/16* | (2016.01) |

(52) U.S. Cl.
CPC .............. *A61K 33/42* (2013.01); *A21D 2/02* (2013.01); *A21D 2/18* (2013.01); *A21D 13/062* (2013.01); *A23L 33/125* (2016.08); *A23L 33/16* (2016.08); *A61K 33/00* (2013.01); *A61K 33/06* (2013.01); *A23V 2002/00* (2013.01); *A23V 2200/328* (2013.01)

(58) Field of Classification Search
CPC ........ A61K 33/42; A61K 33/06; A61K 33/00; A23L 33/125; A23L 33/16
See application file for complete search history.

(56) References Cited

U.S. PATENT DOCUMENTS

| | | | |
|---|---|---|---|
| 6,248,375 B1 | 6/2001 | Gilles et al. | 426/72 |
| 2003/0082287 A1 | 5/2003 | Wolt et al. | 426/549 |
| 2005/0244568 A1 | 11/2005 | Gokhan | 426/658 |
| 2013/0089639 A1 | 4/2013 | Petre et al. | 426/62 |

FOREIGN PATENT DOCUMENTS

| | | | | |
|---|---|---|---|---|
| AU | 2012100061 | | 3/2012 | ............ A21D 2/08 |
| CN | 102228066 | | 11/2011 | ............ A21D 13/00 |
| EP | 2056226 A1 | * | 5/2009 | ............ A61B 5/00 |
| KR | 20110134162 | | 12/2011 | ............ A21D 13/00 |
| WO | WO 07/56802 | | 5/2007 | ............ A21D 2/36 |
| WO | WO-2008113114 A1 | * | 9/2008 | ............ A61K 31/70 |

OTHER PUBLICATIONS

The Peanut Institute (Peanut Nutrition Data, https://peanut-institute.com/peanut-facts/nutritional-breakdown/, copyright 2020) (Year: 2020).*
Eat This Much (Banana, https://www.eatthismuch.com/food/nutrition/banana, 1337/, copyright 2020) (Year: 2020).*
Baum et al (The Journal of Nutrition, 2015, vol. 145, pp. 2229-2235) (Year: 2015).*
Harvard Health Publishing, Glycemic Index for 60+ Foods, https://www.health.harvard.edu/diseases-and-conditions/glycemic-index-and-glycemic-load-for-100-foods, Published Feb. 2015) (Year: 2015).*
Ayoub et al (Nutrition and Diabetes, Dec. 21, 2015, vol. 5, pp. 1-6) (Year: 2015).*
Canadian Living (Calories, Protein, Carbohydrates and Fat: How Much Do I Need?, Jun. 2009) (Year: 2009).*
EP-2056226-A1 (Espacenet English translation, downloaded 2020) (Year: 2020).*
Ayoub, et al., "Effects of phosphorous supplement on weight gain and waist circumference of overweight/obese adults: a randomized clinic trial" *Nutrition and Diabetes* 5(189): 1-6 (2015).
Khattab, et al., "Phosphorus ingestion improves oral glucose tolerance of healthy male subjects: a crossover experiment" *Nutrition Journal* 14(112): 1-8 (2015).
Kattab, et al., "Effect of phosphorous on the oral glucose tolerance test" *Proceedings of the Nutrition Society* 70: p. E60 (2011).
Obeid, et al., "Increased phosphorous content of preload suppresses ad libitum energy intake at subsequent meal" *Int'l Journal of Obesity* 34: pp. 1446-1448 (2010).
Obeid, et al., "Refeeding and metabolic syndromes: two sides of the same coin" *Nutrition and Diabetes* 4(e120): 1-8 (2014).

* cited by examiner

*Primary Examiner* — Mark V Stevens

(74) *Attorney, Agent, or Firm* — J. Peter Paredes; Amin Talati Wasseman LLP

(57) ABSTRACT

Composition and use of macro-minerals to lower postprandial glycemic response and reduce body weight are disclosed herein.

10 Claims, 9 Drawing Sheets

Table 1. Baseline characteristics of the study participants

| Baseline characteristics | Placebo group (n = 21) | Phosphorus group (n = 26) | Unpaired t-test, P-value |
|---|---|---|---|
| Age, mean (s.d.), years | 36.67 (9.76) | 34.04 (11.24) | 0.396 |
| Sex, no. (%) | | | |
| Male | 6 (28.57) | 10 (38.46) | |
| Female | 15 (71.43) | 16 (61.54) | |
| Anthropometric measurements, mean (s.d.) | | | |
| Weight, kg | 92.33 (14.99) | 88.33 (19.14) | 0.426 |
| Height, m | 1.65 (0.08) | 1.66 (0.11) | 0.646 |
| BMI[a] | 33.73 (3.84) | 31.64 (4.64) | 0.099 |
| Waist circumference, cm[b] | 109.43 (9.90) | 106.00 (12.74) | 0.305 |
| Biochemical characteristics, mean (s.d.) | | | |
| Serum phosphorus, mg dl⁻¹ [c] | 79.99 (41.54) | 91.50 (53.20) | 0.540 |
| Total cholesterol, mg dl⁻¹ [d] | 221.85 (40.66) | 216.08 (42.32) | 0.645 |
| LDL-C, mg dl⁻¹ [d] | 143.29 (30.47) | 145.77 (33.50) | 0.797 |
| HDL-C, mg dl⁻¹ [d] | 46.30 (10.98) | 43.12 (11.86) | 0.357 |
| Triglycerides, mg dl⁻¹ [d] | 161.50 (67.60) | 137.40 (81.20) | 0.284 |
| Glucose, mg dl⁻¹ [d] | 95.25 (10.56) | 96.28 (11.37) | 0.755 |
| Insulin, μU ml⁻¹ [d] | 11.41 (7.77) | 7.71 (7.89) | 0.123 |
| HOMA-IR[d] | 2.81 (2.30) | 1.93 (2.27) | 0.210 |
| CRP, mg l⁻¹ [d] | 9.82 (5.51) | 9.40 (3.93) | 0.773 |
| GFR (ml min⁻¹ per 1.73 m²)[d] | 114.14 (10.19) | 112.24 (13.46) | 0.592 |

Abbreviations: BMI, body mass index; CRP, C-reactive protein; GFR, glomerular filtration rate; HDL-C, high-density lipoprotein cholesterol; HOMA-IR, homeostatic model assessment of insulin resistance; LDL-C, low-density lipoprotein cholesterol. SI conversion factor: to convert serum phosphorus to mmol l⁻¹, multiply by 0.323; cholesterol, LDL-C and HDL-C to mmol l⁻¹, multiply by 0.0259; triglycerides to mmol l⁻¹, multiply by 0.0113; glucose to mmol l⁻¹, multiply by 0.0555. [a]Calculated as weight in kg divided by height in m squared. [b]Measured at the midpoint between the lower rib and iliac crest. [c]Because of missing data, based on sample size of 20 and 26 for placebo and phosphorus groups, respectively. [d]Because of missing data, based on sample size of 20 and 25 for placebo and phosphorus groups, respectively.

FIG. 5

Table 2. Changes in anthropometric and biochemical characteristics from baseline to 12 weeks

| Indicator | Placebo group | | | Phosphorus group | | | P-value$^c$, placebo vs phosphorus |
|---|---|---|---|---|---|---|---|
| | Sample size$^b$ | Mean difference (95% CI) | P-value$^c$ | Sample size$^b$ | Mean difference (95% CI) | P-value$^c$ | |
| *Anthropometric measurements* | | | | | | | |
| Weight, kg | 21 | 1.13 (0.19 to 2.06) | 0.02 | 26 | −0.65 (−1.69 to 0.40) | 0.22 | 0.01 |
| BMI$^a$ | 21 | 0.42 (0.05 to 0.78) | 0.03 | 26 | −0.24 (−0.59 to 0.12) | 0.19 | 0.01 |
| Waist circumference, cm$^e$ | 21 | 0.38 (−0.44 to 1.20) | 0.35 | 26 | −3.62 (−4.90 to −2.33) | <0.001 | <0.001 |
| *Biochemical characteristics* | | | | | | | |
| Serum phosphorus, mg dl$^{-1}$ | 20 | 0.163 (0.034 to 0.292) | 0.82 | 26 | −0.111 (−0.299 to 0.077) | 0.78 | 0.017 |
| Total cholesterol, mg dl$^{-1}$ | 20 | −1.00 (−12.83 to 10.83) | 0.86 | 25 | 0.92 (−11.45 to 13.29) | 0.89 | 0.82 |
| LDL-C, mg dl$^{-1}$ | 20 | 2.37 (−10.10 to 14.84) | 0.70 | 25 | 1.43 (−8.71 to 11.58) | 0.77 | 0.90 |
| HDL-C, mg dl$^{-1}$ | 20 | 0.95 (−1.57 to 3.47) | 0.44 | 25 | −0.04 (−3.59 to 3.51) | 0.98 | 0.64 |
| Triglycerides, mg dl$^{-1}$ | 20 | −20.30 (−41.70 to 1.20) | 0.06 | 25 | −2.92 (−21.66 to 15.82) | 0.75 | 0.21 |
| Glucose, mg dl$^{-1}$ | 20 | −1.35 (−5.97 to 3.27) | 0.55 | 25 | 0.64 (−6.98 to 8.26) | 0.86 | 0.65 |
| Insulin, mg dl$^{-1}$ | 20 | −2.61 (−6.52 to 1.29) | 0.18 | 25 | 2.01 (−0.56 to 4.58) | 0.12 | 0.05 |
| HOMA-IR | 20 | −0.77 (−1.89 to 0.35) | 0.17 | 25 | 0.79 (−0.26 to 1.83) | 0.13 | 0.04 |
| CRP, mg dl$^{-1}$ | 20 | 1.25 (−0.65 to 3.15) | 0.19 | 25 | 0.18 (−1.68 to 2.04) | 0.84 | 0.41 |

Abbreviations: BMI, body mass index; CI, confidence interval; CRP, C-reactive protein; HDL-C, high-density lipoprotein cholesterol; HOMA-IR, homeostatic model assessment of insulin resistance; LDL-C, low-density lipoprotein cholesterol. SI conversion factor: to convert serum phosphorus to mmol l$^{-1}$, multiply by 0.323; cholesterol, LDL-C and HDL-C to mmol l$^{-1}$, multiply by 0.0259; triglycerides to mmol l$^{-1}$, multiply by 0.0113; glucose to mmol l$^{-1}$, multiply by 0.0555. $^a$P-value for intergroup comparisons using two-sample t-test. $^b$Based on analysis of patients for whom data were available. $^c$P-values for pairwise intragroup comparisons obtained using paired t-test. $^d$Calculated as weight in kg divided by height in m squared. $^e$Measured at the midpoint between the lower rib and iliac crest.

FIG. 6

Table 3. Changes in subjective appetite scores from baseline to 12 weeks

| Variable | Group | Sample size (n) | Mean difference (95% CI) 6 weeks | Mean difference (95% CI) 12 weeks | P-value Time | P-value Treatment | P-value Time × treatment |
|---|---|---|---|---|---|---|---|
| Appetite | Placebo | 21 | −0.33 (−0.77 to 0.11) | −0.24 (−0.67 to 0.19) | 0.002 | 0.01 | 0.18 |
|  | Phosphorus | 26 | −0.92 (−1.38 to −0.47) | −0.73 (−1.24 to −0.23) |  |  |  |
| Quantity of food to reach fullness | Placebo | 21 | −0.57 (−0.94 to −0.20) | −0.33 (−0.77 to 0.11) | <0.001 | 0.04 | 0.30 |
|  | Phosphorus | 26 | −0.85 (−1.24 to −0.46) | −0.81 (−1.25 to −0.37) |  |  |  |
| Hunger | Placebo | 21 | −0.62 (−1.09 to −0.15) | −0.33 (−0.75 to 0.08) | <0.001 | 0.31 | 0.53 |
|  | Phosphorus | 26 | −0.73 (−1.15 to −0.31) | −0.73 (−1.12 to −0.34) |  |  |  |
| Taste of food | Placebo | 21 | 0.00 (−0.20 to 0.20) | −0.05 (−0.32 to 0.22) | 0.09 | 0.007 | 0.18 |
|  | Phosphorus | 26 | −0.31 (−0.56 to −0.06) | −0.35 (−0.60 to −0.09) |  |  |  |
| Number of main meals | Placebo | 21 | 0.14 (−0.08 to 0.36) | 0.19 (0.01 to 0.37) | 0.76 | 0.59 | 0.90 |
|  | Phosphorus | 26 | 0.08 (−0.47 to 0.62) | 0.04 (−0.50 to 0.58) |  |  |  |
| Number of snacks | Placebo | 21 | −1.90 (−0.61 to 0.23) | −0.10 (−0.55 to 0.36) | 0.04 | 0.01 | 0.21 |
|  | Phosphorus | 26 | −0.81 (−1.33 to −0.28) | −0.81 (−1.39 to −0.23) |  |  |  |

Abbreviation: CI, confidence interval. [a]P-values for repeated measures analysis of variance (ANOVA).

FIG. 7

COMPOSITION AND USE OF MACRO-MINERALS TO LOWER POSTPRANDIAL GLYCEMIC RESPONSE AND REDUCE BODY WEIGHT

CROSS-REFERENCE TO RELATED APPLICATIONS

The present application is a divisional application from U.S. application Ser. No. 15/459,412, filed Mar. 15, 2017, which claims priority from U.S. Provisional Application Ser. No. 62/308,546, filed Mar. 15, 2016, all herein incorporated by reference in their entireties.

BACKGROUND

The invention generally relates to food products, more specifically bread products.

Postprandial glycaemia or glycemic index (GI) is known to be positively associated with the development of diabetes and obesity. The latter is also the result of imbalance between energy intake and expenditure. Furthermore, intake of refined carbohydrates (e.g. made from white wheat flour, white rice and byproducts, sugar, sweeteners, etc.) is positively associated with the development of obesity and diabetes. The availability of refined carbohydrates increased tremendously during the past few decades due to modernization and its related factors; including industrialization and globalization of food markets, and refined carbohydrates seem to contribute to more than 50% of the food supply (kcal per capita per day) in most countries. Thus, there is a paramount need to uncover the detrimental potential of refined carbohydrates. Refinement of grains removes a large percentage of their vitamin and mineral contents (around 70%). However, many countries tend to enrich their white flour with several vitamins, known to be involved in carbohydrate metabolism (e.g. thiamin, riboflavin and niacin). While enrichment with minerals; especially macro-minerals, has been ignored despite their ultimate importance.

On the other hand, most studies on obesity were mainly focused on the intake and metabolism of macronutrients (carbohydrates, proteins and fats), though their absorbed forms (type of fatty acids, amino acids, glucose, etc.) are not believed to have been drastically altered, in contrast to that of micronutrients.

The present invention solves these problems as well as others.

SUMMARY OF THE INVENTION

Provided herein are compositions and use of macro-minerals to lower postprandial glycemic response and reduce body weight. A formulation of food products supplemented with macro-minerals is disclosed and generally comprises: a food product including a carbohydrate that lowers the glycemic response including Phosphorus (P) at an active concentration.

A method of preventing weight gain and reducing waist circumference is disclosed and generally comprises: delivering at least between about 300 mg to about 500 mg of phosphorus with each meal, wherein each meal include about 300 to about 500 Kcal of carbohydrate over a period of time and increasing energy expenditure.

A method of enriching a bread product is generally disclosed and comprises: restoring the levels of phosphorus (P), potassium (K), and magnesium (Mg) prior to processing and milling, whereby each Kg of white flour contained between about 2.0 and 5.0 g of Mg and between about 5.0 and about 10.0 g of K and P; and fortifying the bread product to double the premilling levels of phosphorus (P), potassium (K), and magnesium (Mg).

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 5 is a Table showing the baseline characteristics of the study participants.

FIG. 6 is a Table showing the changes in anthropometric and biochemical characteristics from baseline to 12 weeks.

FIG. 7 is a Table showing the changes in subjective appetite scores from baseline to 12 weeks.

DETAILED DESCRIPTION OF THE INVENTION

Figure 1A:
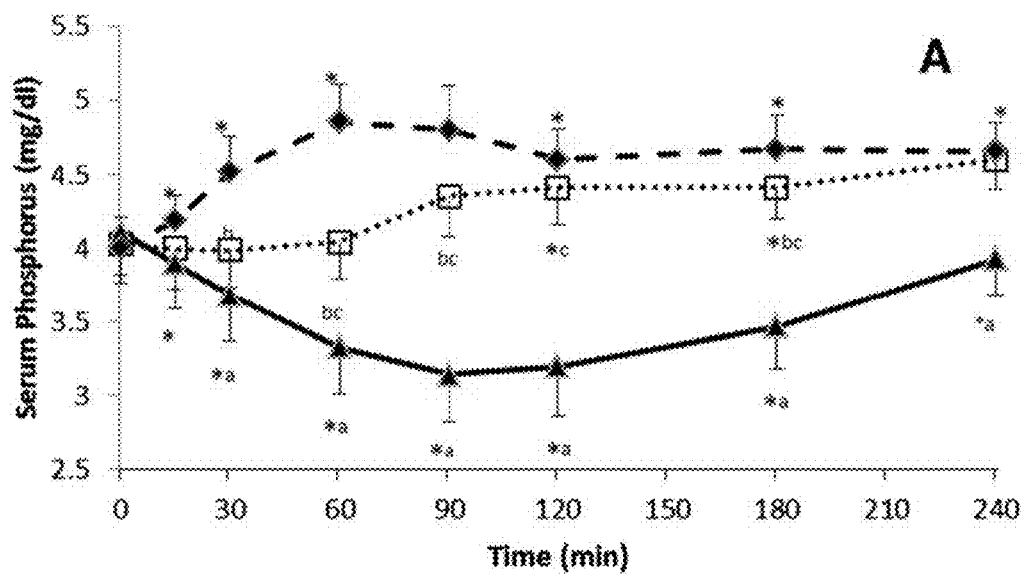
FIGS. 1A-1C are graphs showing the Changes in Serum Phosphorus (a), Glucose (b) and Insulin (c) levels of subjects in experiment 1; # Experiment 1: After the ingestion of 500 mg phosphorus (-♦-), 75 g glucose (- ▲ -) or co-ingestion glucose+phosphorus (75 g glucose+500 mg of phosphorus) (..□..), where * p-value<0.05: Paired t-test in the same treatment in comparison with baseline (time 0) value, where FIG. 1A has a p-value<0.05: Paired t-Test, phosphorus vs glucose treatments at each time point, where FIG. 1B the p-value<0.05: Paired t-Test, phosphorus vs glucose+phosphorus treatments at each time point, where FIG. 1C the p-value<0.05: Paired t-Test, glucose vs glucose+phosphorus treatments at each time point.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and nutraceutical, and food arts.

Phosphorus is essential for the metabolism of carbohydrates (glucose), especially for the intracellular trapping of glucose. The entrapment of glucose thus induces several desired effects including: 1) Glucose is out of the blood circulation, 2) Energy or ATP can then be released, 3) With the attainment of energy, the body no more feels the need for food intake and thus experiences a state of suppressed appetite.

In humans, the availability of free phosphorus is limited and this creates a competition between different metabolic processes that require phosphorus. Such competition is believed to compromise the activities of several metabolic processes especially in the postprandial status when the need is heightened. The present invention comprises carbohydrate ingestion (glucose) accompanied by exogenous availability of phosphorus in order to fulfill the requirement of all metabolic processes and such availability would improve postprandial glycaemia and decrease body weight. A reduced glycemic index is a glycemic index value that is at least 5% lower after ingestion of an equivalently sweet amount of sweetener in a product as described herein relative to the index of a given amount of sucrose when ingested as refined sucrose. The reduction in glycemic index is preferably greater, e.g., about 10%, 20%, 30%, 40%, 50%, 60%, 70%, 80%, 90% or more.

In one embodiment, phosphorus compounds are added to food products as to increase the phosphorus percentage by at least about 50% to about 500%, or potassium compounds are added to food products to increase the potassium percentage by at least 50% to about 500%, or magnesium compounds are added to food products to increase the magnesium percentage by at least 50% to about 500%. Alternatively, potassium compounds can be delivered in form of supplements to be added to food products in order to exert its beneficial effect. Supplements may take the form of tablets, pills, sachets, capsules, powders, liquid forms.

Phosphorus alone or with magnesium and potassium can be used to enrich (fortify) refined carbohydrates, food products, bread products, and their byproducts (wheat flour and products, sugar sweeteners, corn flour and products, white rice and products). Phosphorus compounds may be added in the amounts of between about 500 mg per 500 kcal carbohydrate meal.

The present invention comprises the addition of phosphors to an oral glucose load to improve postprandial insulin sensitivity (decreasing the postprandial serum glucose concentration and postprandial insulin concentration, Example 1). The addition of phosphorus may be in the form of potassium phosphate in the amount between about 100 mg and about 500 mg in a tablet or pill form. In one embodiment the present invention comprises ingesting phosphorus compounds at least between about 30 minutes to about 90 minutes before eating or ingesting any glucose. The decrease of postprandial serum glucose concentration may be between about 2 and 10 mg/dl. The decrease in serum glucose levels occurs during a time period. The decrease in serum insulin may between about 10 µU/ml and 40 µU/ml. The increase in insulin sensitivity may between about 7.00 and 20.00 according to the insulin sensitive index.

The present invention comprises the addition of phosphorus to carbohydrate preloads was able to decrease subsequent energy intake (Example 2). The present invention comprises the addition of between about 100 mg and 600 mg of phosphorus to a solution and taken before a meal. In one embodiment, the phosphorus is a mixture of potassium and sodium phosphate. In one embodiment, the time before the meal is between about 30 and 90 minutes. The addition of phosphorus to the water preload may comprise at least between about a 10% to a 40% reduction in energy intake at the subsequent meal, and at least between about a 10% to 40% reduction in glucose, while the addition of phosphorus to the sucrose or fructose preloads comprises at least between about a 10% to 40% reduction in energy intake at the subsequent meal.

The present invention comprises the addition of phosphorus to a high carbohydrate meal was able to increase and prolong postprandial thermogenesis (energy expenditure) which was, interestingly, caused by an increase in fat oxidation (Example 3).

The present invention comprises the ingestion of phosphorus tablets with the main meals (breakfast, lunch and dinner) for at least 12 weeks to reduce weight and waist circumference, and to decrease appetite (Example 4). The present invention comprises the ingestion of at least between about 300 mg to about 500 mg of phosphorus with each meal, wherein each meal include about 300 to about 500 Kcal of carbohydrate (or about 1 mg of phosphorus per 1 Kcal from refined carbohydrate) over a period of time prevents weight gain and reduce waist circumference among overweight and obese adults. The period of time may be between about 10 weeks to about 15 weeks. An overweight adult is an adult between the ages of 18 to 45 with a Body Mass Index<25 kg/m$^2$. The decrease in body weight may be between about 0.40 kg to about 0.80 kg. The decrease in the waist circumference is between about 2.00 cm to about 5.00 cm. The serum levels of phosphorus during the time period will not be affected. The decrease in appetite may be between about −0.4 to about −1.5.

The present invention comprises the production of a bread product (Example 5) from flour enriched with phosphorus (P) plus two other macronutrients potassium (K) and magnesium (Mg), which are depleted during the process of flour milling at two levels. A first level is to restore the original levels of phosphorus (P), potassium (K), and magnesium (Mg) (prior to processing and milling), whereby each Kg of white flour contained between about 2.0 and 5.0 g MgCO$_3$ and between about 5.0 and about 10.0 g of KH$_2$PO$_4$. Another level was fortified bread product to double the premilling levels of phosphorus (P), potassium (K), and magnesium (Mg). In one embodiment, the fortification comprises each Kg of white flour containing between about 5.0 and about 10 g of MgCO$_3$ and between about 20 and about 30 g of KH$_2$PO$_4$. In one embodiment, phosphorus compounds are added to bread products as to increase the phosphorus percentage by at least about 50% to about 500%, or potassium compounds are added to bread products to increase the potassium percentage by at least 50% to about 500%, or magnesium compounds are added to bread products to increase the magnesium percentage by at least 50% to about 500%. The present invention a) Reduced postprandial glycaemia between about 20% and 40% (GI) as compared to white pita bread whereby Postprandial serum glucose change is lower between about 20% and 40% than that of regular bread products at 60 minutes onwards; b) maintained low levels of postprandial plasma triglycerides between about −5 mg/dl and about −20 mg/dl; and c) palatability of pita bread was not affected by the addition of macrominerals. Maintained similar sensory characteristics using triangle difference and acceptability tests.

The present invention comprises phosphorus' co-ingestion with refined carbohydrates improves postprandial glycaemia, increase energy expenditure, decrease appetite and decrease body weight. Moreover, its addition to bread did not affect the sensory properties and palatability. The levels of phosphorus used, whether in the form of tablets or enrichment of bread, have marginal effects on the production costs of bread and its byproducts. Moreover, the daily ingestion of about 500 g (2000 Kcal) of the enriched bread, though the average USA daily wheat flour consumption per capita is about 160 g, would be lower than the upper limit of intake (4000 mg per day) set by different health agencies/organizations including institute of medicine (IOM).

The present invention comprises: 1) decreasing postprandial glycemia through improving insulin sensitivity), 2) increasing energy expenditure and 3) suppressing appetite. Consequently, the present invention produces better glycemic and weight control and enhances the health and well-being of populations.

The present invention comprises enrichment of refined carbohydrates or the ingestion of phosphorus tablets or sachets with refined carbohydrate meals. The present invention comprises the enrichment of refined carbohydrates that includes a high level of adherence due to their marginal effects on palatability of foods and dietary practices/habits of populations.

The present invention improves the health status of subjects by curbing the detrimental effects of refined carbohydrates comprising: 1) Lowers postprandial glycemic response of refined carbohydrates; 2) Increases energy expenditure following ingestion of refined carbohydrates; and 3) Decreases appetite; and 4) Reduces body weight of subjects.

The present invention comprises: 1) targeting of the general population; 2) ensuring high compliance, when used as fortificant for refined carbohydrates given that they are highly consumed on regular basis (e.g. bread is a staple item in most peoples' diets); 3) delivering effects through the use of an essential nutrient and within the normal range of requirement (dietary reference intake, i.e. a nutritional not pharmacological dose); 4) providing an approach for reducing postprandial glycemia, appetite and body weight, as well as increasing postprandial thermogenesis; 5) not affecting the characteristics of bread and, therefore, would not require dietary changes; 6) minimally affecting the production costs of refined carbohydrates e.g. bread; 7) incorporating into food (e.g. bread) that has no effect on palatability and sensory properties.

The present invention decreases weight and waist circumference and causes removal of fat rather than loss of lean body mass, especially since the increase in energy expenditure was mainly related to an increase in fat oxidation. Therefore, the effect of phosphorus on body composition and protein synthesis is shown. In addition, the impact of phosphorus addition on several components of the metabolic syndrome especially among subjects with an existing metabolic syndrome. The palatability and sensory properties of other refined carbohydrates and their byproducts (especially white rice and byproducts since it is staple food in many countries) is not affected by the present invention.

The reduction of an excessive body fat causes effect to treat, improve and prevent a disease the cause of which is said to be corpulence or excess of body weight, for example diabetes, arteriosclerosis, hyperpiesia, cancer, hyperlipemia, ryeumatism, hyperrucicemia, arthritis deformans, gout, cerebral accident, ischemic heart disease, respiratory injury, pancreatitis, cataract, Alzheimer's disease, allergic disease, aging, hidrosis, ischemic disease, complications of diabetes being kidney disease, nerve injury and retinopathy.

This invention has successfully identified the potential beneficial role of minerals in improving the glycemic response of white bread and overall glucose control in healthy male subjects. For the present invention, sensory results did not indicate any major effect of the experimental treatments on the quality of the bread, which is an encouraging outcome and indicative of the tolerance of bread quality to the addition of P, K and Mg.

Formulating a white bread supplemented with the proper levels of macro-minerals, as shown in this work/invention could be of huge value to the glycemic response of this staple food and could serve as a model for other food products with high postprandial glycemic response, thereby lowering postprandial glycaemia of peoples' diets, an essential step and a major preventive measure for several non-communicable diseases.

Phosphorus may take the form of phosphorus-based acids, Monopotassium phosphate, any phosphates (compounds containing the phosphate ion, $PO_4^{-3}$), phospholipids, soluble salts of potassium, bisphosphonate, a hydroxybisphosphonate, a phosphonate, a phosphate, an aminomrnethylenephosphonic acid, and an acidic peptide. Polyphosphonic acids and aminomethylenephosphonic acids have a high affinity for bone in vivo due to their binding of the exposed calcium ions in hydroxyapatite (calcium phosphate), and also are suitable for use in the context of the present methods. The terms "phosphonate, phosphate, and aminomethylenephosphonate" are meant to encompass the phosphonic acids, the phosphoric acids, and aminomethylenephosphonic acids, respectively, as well as any salts, hydrolyzable esters, and prodrugs of the phosphorous-based acids thereof. Therefore, the phosphonic acid, phosphoric acid, and aminomethylenephosphonic acid are drawn and utilized interchangeably with phosphate, phosphonate, and aminomethylenephosphonate. Biologically hydrolyzable esters of the phosphorus-based acids may also be utilized in the method of the invention.

As used herein, the term "active concentration" refers to a quantity sufficient to achieve a desired therapeutic and/or prophylactic effect, e.g., 1) Lowers postprandial glycemic response of refined carbohydrates; 2) Increases energy expenditure following ingestion of refined carbohydrates; and 3) Decreases appetite; and 4) Reduces body weight of subjects.

Definitions

The glycemic index is the extent to which blood sugar is increased upon ingestion. A "reduced" glycemic index is a glycemic index value that is at least 5% lower after ingestion of an equivalently sweet amount of sweetener in a product as described herein relative to the index of a given amount of sucrose when ingested as refined sucrose. The reduction in glycemic index is preferably greater, e.g., 10%, 20%, 30%, 40%, 50%, 60%, 70%, 80%, 90% or more, relative to enriched carbohydrates.

Preferably, in an enriched carbohydrate according to the invention, the flour comprises (or consists of) cereal flours. More preferably, the flour for use in a bread product according to the invention is selected from the group consisting of wheat flour, whole wheat flour, complete (wheat) flour, (whole) oat flour, (whole) spelt flour, and mixtures thereof. Even more preferably, the flour for use in a bread product according to the invention is selected from the group consisting of wheat flour, whole wheat flour, complete wheat flour, and mixtures thereof.

Flour—White flour contains substantially only ground endosperm of the wheat kernel, and includes very little or none of the bran, the outer covering of the grain, and the grain contained inside the kernel.

Whole wheat flour by contrast contains a reconstituted material where the separated bran, grain and endosperm are recombined to give a flour of high bran content. It is worth noting, however, that the amount of bran in white flour varies from country to country. The level of bran in flour is usually quantified by measuring ash content. The ash content in white flour may vary between about 0.3% to around 1%. For example, in the USA and China the ash content is usually about 0.4% and in Australia it is usually in the range of 0.5% to 0.7%. In contrast, whole meal flours in Australia have a higher ash content usually in the range of 1.1% to 1.4%.

Soluble fiber—Carbohydrate which is not digestible by the human digestive tract, but is fermented by gut bacteria.

White flour contains the ground endosperm of the grain and is a white, pure flour with the bulk of the bran or germ of the grain removed such that the ash content of the flour is usually less than 0.75%, preferably less than 0.70% and even more preferably less than 0.66%. This is in distinct contrast to whole wheat flour, otherwise known as whole meal flour, which contains all of the bran and germ content of the flour grain. The white flour used in the present invention preferably has a particle size less than about 600 µm, more preferably between about 90 µm to about 500 µm, or mixtures of flours within those ranges. Flour having a particle size of about 500 µm is generally referred to as semolina. The white flour (e.g. baker's wheat flour) used in this invention may contain from 0 to 100% semolina, such as 10% to 100%, 20% to 100%, 30% to 100%, 40% to 100%, 50% to 100%, 60% to 100%, 70% to 100%, 80% to 100%, 90% to 100% and 100% semolina. White flour such as standard baker's wheat flour generally has a particle size of between about 90 µm and 180 µm, and such flour may be utilized, or mixtures thereof with semolina in proportions already mentioned, or mixtures of white flour having a particle size generally from about 180 µm to about 500 µm.

If semolina is incorporated within the product it may be necessary to alter proportions of other components, for example because relative to standard baker's wheat flour the semolina absorbs less water. In this case it may be appropriate to add additional non-starch polysaccharide, which increases water absorption.

Non-starch polysaccharides include one or more polysaccharides, such as a mixture of two or more non-starch polysaccharides. Non-starch polysaccharides according to the present invention are food grade non-starch polysaccharides, including processed forms of gums, plant and microbial polysaccharide extracts, polysaccharide extracts from grains (such as barley, oats), and polysaccharide extracts from seaweeds, all of which are widely commercially available and find various diverse uses in the food industry. Non-starch polysaccharides include, but are not limited to, guar, pectins, hemicelluloses, alginates, xanthans, locust bean gum, tragacanth, *psyllium*, arabic, acacia, gellan, glucans such as β-glucan, carrageenans, oat and barley fibre. Non-starch polysaccharides are preferably added in appropriate quantity to give an amount of about 0.5% to 6%, preferably 1% to 6%, more preferably 1% to 4% of a baked white bread product.

The white bread product comprises a soluble fibre content of at least about 0.5% on a 40% water content basis, this being the total moisture content of the baked bread product, preferably 0.5% to 4%, more preferably 1% to 3%, and still more preferably 1% to 2.5%. Soluble fibre content of the baked bread may be determined for example by the method of AOAC 32.1.17 Official Method 991.43 ($17^{th}$ Ed, 2000), Association of Official Analytical Chemists, Washington D.C., USA.

Edible fats (including edible fats, oils and lipids and lipid containing or mimicking agents) are widely used in the baking industry and these include vegetable oils, (including canola, soy, corn, olive, palm, coconut, and peanut), hydrogenated fats, butter, margarine, tallow, lard, eggs, marine oils (eg. fish oils), emulsifiers, fat mimics, hydrated monoglycerides and mixtures thereof. The edible fat (including fat present in other ingredients of the product such as the flour) is present in the white bread product in an amount between 0 and 8%, preferably about 0.5% to about 5%, preferably 0.5% to 3% and most preferably greater than about 2.1%. For example, the total amount of edible fat within the baked product can be determined by the technique of solvent extraction with acid hydrolysis (see AOAC Official methods, 922.006, 945.44 ($17^{th}$ Ed, first revision, 2002), Association of Official Analytical Chemists, Washington D.C., USA).

Maltose content of a baked bread product, such as a baked white bread product, is a measure of enzymic digestion during the bread making process. The white bread product according to the present invention has a maltose content of less than about 5%, for example from about 0.5% to about 5%, 0.5% to about 4.5%, 1% to about 3.5. A figure of about 5% or less maltose content is indicative of significant amylolytic enzymic degradation during the bread manufacturing process. For example the maltose content of the baked product can be determined by high performance liquid chromatography (HPLC) (see AACC Method 80-04 ($10^{th}$ Ed, 2000), American Association of Cereal Chemistry, St. Paul, Minn., USA or AOAC 44.4.13, Official Method, 977.20 ($17^{th}$ Ed, second revision, 2003), Association of Official Analytical Chemists, Washington D.C., USA).

The specific volume of a loaf of bread or bakery product is a measure of the density of the crumb of the bakery product, particularly a loaf of bread. White bread is characterized by a light and fluffy crumb, associated with a high volume expanded crumb. The volume of a loaf of bread or more properly its specific volume is measured as the volume of the loaf divided by weight of bread. The specific volume of the bread product according to the present invention is from 3 to 9 cm³/g, more preferably between 4 to 6 cm³/g, which is characteristic of a light and fluffy high volume white bread product. Bread product specific volume is readily calculated as: volume (cm³)/weight (g). Volume can be determined by image analysis or seed displacement, for example.

The crumb of the baked white bread is white. That is, it has a generally white appearance and to the naked eye is generally visibly free from bran specks, nuts, seeds and grains. In a preferred embodiment, the crumb of the baked bread of the invention has a CIE L*-b* value, such as measured using the HunterLab CIE colour scale (HunterLab, Insight on Color, Jul. 1-15, 1996, Vol. 8, No. 7), greater than 66, more preferably between 68 and 74; as characteristic of a demonstrably visible white bread. Hence, the colour of the white bread product is fully consonant with the white bread texture, taste and appearance.

The white bread product according to the invention has a lowered GI of about 65 or less, preferably a low GI of 55 or less, and more preferably a GI of between about 45 and about 55. For example, GI of the bread can be determined by adopting the Standards Australia draft standard DR 05435.

The low GI white bread according to the present invention retains its low GI status when manufactured in a modern continuous baking process.

The white bread product of the present invention has significant softness after production, for example, with examples of the softness of the bread of the invention including a softness of about 0.8-2 N, preferably 1-1.2 N on one day of shelf life, and a softness of about 2-3 N, preferably 2-2.5 N on five days of shelf life, following packaging in a typical polythene bag. Softness can for example be measured by force penetration using a Stable Microsystems Texture Analyser TaTx2 and a 36 mm aluminum cylindrical probe which measures breadcrumb firmness by determining the force required to compress a product a specified distance (parameters: test speed 0.3 mm/sec, distance 10 mm and sample thickness 25 mm).

The white bread product includes but is not limited to square, lidded tin breads, unlidded breads such as high top breads, and free standing breads such as cobs and viennas, rolls, bagels, hamburger buns, baguettes, Italian and Turkish style breads such as foccacia ciabatta and pide, and Asian style breads such as steamed buns.

The bread composition preferably contains standard suitable bread ingredients, including yeast, wheat gluten, salt, soy flour, vitamins, minerals, gluten and other proteins, antioxidants, sweeteners and emulsifiers. If desired, dough conditioners (such as enzymes) and/or preservatives can be included in the bread composition, as it will be understood by one of ordinary skill in the art.

The baked bread product in accordance with this invention may be made by standard bread manufacturing means, including the conventional sponge and dough methodology, and straight dough methodology, particularly manufactured in a standard continuous baking process. The sponge and dough method may produce breads with an improved flavour and improved shelf-life characteristics compared to breads made by the straight dough method.

In the sponge and dough method, a two-stage mixing process is used. First, part of the ingredients (a portion of the total flour, yeast and water) of a bread composition are mixed to form a "sponge" and allowed to ferment for an appropriate time, such as 3 to 4 hours at 20° C. at atmospheric or controlled humidity (such as 80% to 90% relative humidity). After the sponge fermentation stage is completed, the remainder of the ingredients are added to the sponge, and a dough is then formed by mixing. The dough is mixed at a suitable speed and for a suitable time to develop the dough product. Following a rest period, the dough is mechanically divided into pieces, rounded and machine molded. The molded dough pieces are placed in an appropriate container for the respective dough weight, and proved at around 25° C. to 45° C. and 70% to 90% humidity. After appropriate proving to give the appropriate height for the given container, the containers are loaded into an oven and baked at 200° C. to 230° C. for about 20 to 30 minutes, this depending on the weight of the dough and the oven type, and bread form, as would be understood by one skilled in the art. Following baking the bread is removed from the container and allowed to cool, for example for 1 to 2 hours, before being bagged.

In the straight dough process, all of the ingredients for the bread are mixed into a dough in a single mixing step without formation of a sponge. The dough is fermented for a suitable period of time, such as from about 20 minutes to about 20 hours, more preferably about 1-4 hours. The dough is then divided, weighed and processed as described above for the sponge and dough method.

It is possible for the dough to be chilled or frozen before baking. Such dough can be transported from one site to another for baking or may be made available to consumers in the form of a chilled or frozen dough, such that the consumer can then bake the bread at a convenient time to thereby enjoy fresh baked bread. The present invention encompasses the preferably chilled or frozen dough composition and methods of producing the dough and the baked bread product.

Two pita bread formulations viz. restored white pita bread (RWPB; to restore its pre-milling levels) and fortified white pita bread (FWPB; to double its pre-milling levels) with macro minerals (P, K, Mg) were prepared and their sensory properties and postprandial glycaemia compared to those of white pita bread (WPB). The sensory characteristics of breads were assessed using a triangle difference test and an acceptability test. Postprandial glycaemia was determined using a single blinded cross over design whereby overnight-fasted healthy male subjects consumed in random order one of the 3 different types of pita bread. Palatability of pita bread was not affected by the addition of macro-minerals, while postprandial glycaemia of RWPB and FWPB were significantly lower than that of WPB at 60 minutes onwards. Additionally, RWPB and FWPB breads maintained low levels of postprandial plasma triglycerides as compared to WPB. Among the bread types, FWPB significantly retained the lowest GI compared to WPB. These findings indicate that the postprandial glycaemia of whole wheat may be attributed to its content of macro minerals. At these levels of addition, the minerals (P, K, Mg) would have marginal effects on the production costs of pita bread and ingestion of about 500 g (2000 Kcal) per day would be lower than the upper limit of intake set by different health agencies/organizations including institute of medicine (IOM).

As used herein, a "food product" is a food in a form that does not exist in nature. In embodiments, a food product includes at least two edible ingredients that do not exist together in nature. A "food" is a nutritious substance that animals, including humans, pets and livestock, eat or drink. A "nutritious substance" is a macronutrient such as a fat, carbohydrate or protein, or a micronutrient such as an essential or non-essential vitamin or mineral.

One or more phosphorous compounds described herein or derivatives thereof, alone or in combination, may be incorporated into a food product. The one or more compounds may elicit a perception of saltiness when the food product is consumed. In embodiments, the one or more compounds are included in a food product that contains a salt that imparts a salty taste. Preferably, at least one of the one or more compounds is a taste modulating compound or salty taste modulating compound.

In embodiments, a food product includes an ingredient, a salt that imparts a salty taste, and a taste modulating or salty taste modulating compound. The ingredient may be a nutritious ingredient; that is, an ingredient that is a nutritious substance. The taste modulating or salty taste modulating compound may be present in the food product in an amount sufficient to enhance the salty taste of the food product. In embodiments, the ingredient, the salt and the taste modulating or salty taste modulating compound are present in the food product in amounts or concentrations not found in naturally existing food products, such as bananas, peppers, avocadoes, wheat, or the like.

Hereinafter, the present invention is more specifically described by way of examples; however, the present invention is by no means limited thereto, and various applications are possible without departing from the technical idea of the present invention.

EXAMPLES

Example 1: Phosphorus Ingestion Improves Oral Glucose Tolerance of Healthy Male Subjects The example was comprised of two experiments. Healthy male subjects were recruited to perform the experiments (Table 1). Placebo (cellulose) or P (125 mg of potassium phosphate per tablet) tablets, which had similar weight and color, were administered to subjects in a randomized order to prevent order-of-treatment effect. The consent forms were obtained from patients.

TABLE 1

Characteristics of the study subjects

| Characteristics | Mean ± SEM |
| --- | --- |
| Experiment 1 (n = 7) | |
| Age (years) | 23.22 ± 1.83 |
| Weight (kg) | 68.88 ± 4.05 |
| Height (m) | 1.74 ± 0.02 |
| BMT (kg/m$^2$) | 22.65 ± 0.82 |
| Fasting glucose (mg/dl) | 86.38 ± 1.62 |
| Fasting triglycerides (mg/dl) | 90.63 ± 15.9 |
| Fasting phosphorus (mg/dl) | 4.06 ± 0.19 |
| Experiment 2 (n = 8) | |
| Age (years) | 27.3 ± 1.68 |
| Weight (kg) | 73 ± 4.78 |
| Height (m) | 1.76 ± 0.04 |
| BMT (kg/m$^2$) | 23.5 ± 0.97 |
| Fasting glucose (mg/dl) | 88 ± 2.17 |
| Fasting triglycerides (mg/dl) | 119 ± 15.3 |
| Fasting phosphorus (mg/dl) | 3.75 ± 0.2 |

Experiment 1: The Effect of Phosphorus Ingestion on Oral Glucose Tolerance Test [OGTT]

Seven overnight fasted subjects (age (mean±SEM): 23.2±1.83 years; BMI: 22.65±0.82 kg/m2) (Table 1: Experiment 1) were asked to attend 3 experimental sessions that were separated by a minimum of 3 days. Sessions included the consumption of either 500 mg of P (4 tablets), a glucose solution (75 g glucose) with 4 Placebo tablets, or a glucose solution (75 g glucose) with 500 mg P. All were ingested with 250 ml of cold water. Blood was withdrawn at base-line and monitored till 240 min (min) after consumption.

Experiment 2: The Effect of Pre-Phosphorus Ingestion on OGTT

Based on data from experiment 1, peak serum P concentration (60 min) was associated with significant decrease in serum glucose and insulin levels. Thus, experiment 2 was designed to investigate whether P intake one hour prior to glucose ingestion would potentiate the effect of P on postprandial glucose and insulin levels. Eight over-night fasted subjects (age: 27.3±1.68 years; BMI: 23.5±0.97 kg/m$^2$) (Table 1: Experiment 2) attended 2 experimental sessions that were separated by a minimum of 3 days. Subjects were given placebo or P (500 mg) tab-lets 60 min prior to glucose ingestion. Blood was drawn at baseline (−60 min) and monitored till 240 min relative to glucose ingestion.

Serum was separated from collected blood samples and stored at −80° C. for later analysis of glucose, total P, tri-glyceride and insulin. Glucose was measured from venous samples. Insulin sensitivity was estimated by the method of Caumo A, Bergman R N, Cobelli C. Insulin sensitivity from meal tolerance tests in normal subjects: a minimal model index. J Clin. Endocrinol. Metab. 2000; 85:4396-402 and expressed as $(\times 10^4 \, dl \cdot kg^{-1} \cdot min^{-1} \cdot \mu Uml^{-1})$. The method is based on the kinetic of both glucose and insulin through coupling their rate of appearance into circulation following oral glucose ingestion. It is based on simple area under the curve type of calculation and was validated in normal subjects in whom their calculated insulin sensitivity was strongly correlated to that of frequently formula sampled IV glucose test (FSIGT). In addition, index of insulin sensitivity was calculated using the composite equation proposed by Matsuda M, DeFronzo R A. Insulin sensitivity indices obtained from oral glucose tolerance testing: comparison with the euglycemic insulin clamp. Diabetes Care. 1999; 22 (9):1462-7.

Data are presented as means±SEM. Paired t-tests were used to compare between treatments and to detect the difference from baseline within each treatment. Repeated Measure ANOVA was run to test the effect of treatment groups over time on each of the dependent variables (P, Glucose and insulin). The level of significance was fixed at P <0.05.

Baseline serum levels of the different parameters (total P, glucose, insulin) were similar between sessions and both experiments (Table 1).

Ingestion of P alone increased serum P significantly, while ingestion of glucose alone decreased postprandial serum P levels. The pattern of serum P changes following glucose and P ingestion (G+P) was different than that of the other two treatments (FIG. 1a), in line, repeated measures ANOVA showed that serum P was significant according to treatment (Table 2: Experiment 1).

TABLE 2

Repeated measure ANOVA outcome variables (Phosphorus, glucose and Insulin) of the two experiments

| Outcome variables | Time (P value) | Treatment (P value) | Interaction (P value) |
| --- | --- | --- | --- |
| Experiment 1 (n = 7)$^a$ | | | |
| Serum Phosphorus | 0.616 | 0.000 | 0.321 |
| Serum Glucose | 0.000 | 0.145 | 0.207 |
| Serum Insulin | 0.000 | 0.168 | 0.619 |
| Experiment 2 (n = 8) | | | |
| Serum Phosphorus | 0.001 | 0.002 | 0.498 |
| Serum Glucose | 0.000 | 0.815 | 0.961 |
| Serum Insulin | 0.000 | 0.233 | 0.724 |

$^a$Only glucose with placebo and glucose with P groups were included in the analysis.

Figure 1B:
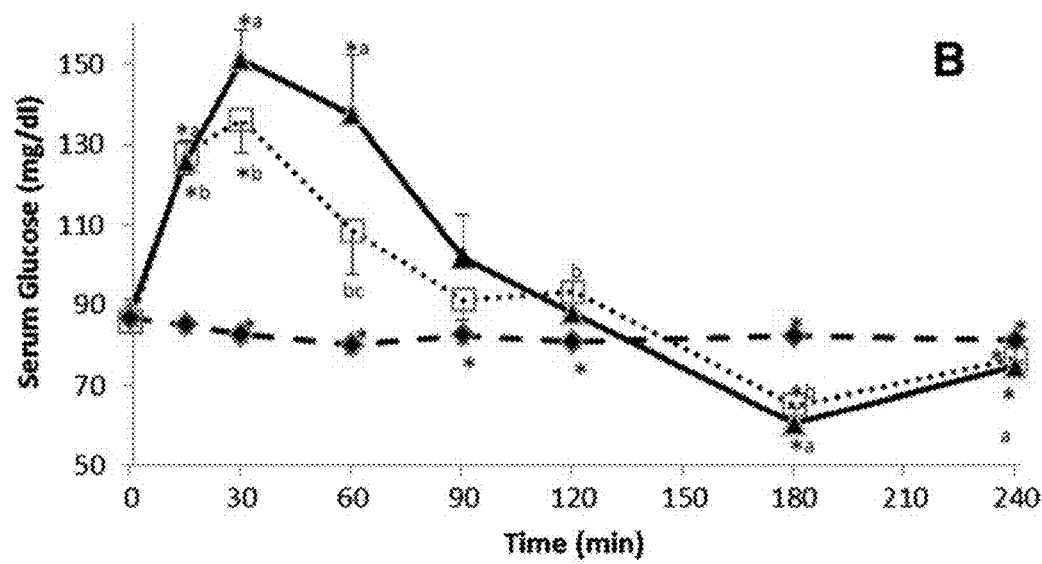

Postprandial serum glucose concentration of the P treatment group significantly decreased by around 5 mg/dl during the experimental session, but this minimal reduction is believed to be the result of fasting. Glucose ingestion increased postprandial serum glucose levels of both treatments, glucose and G+P, but the magnitude of the increase was significantly lower in the G+P as compared to glucose treatment at time 60 min (P=0.016), (FIG. 1b). Repeated measures ANOVA showed that serum glucose levels were significantly different according to time, but failed to reach statistical significance between treatments (Table 2: Experiment 1).

Figure 1C:
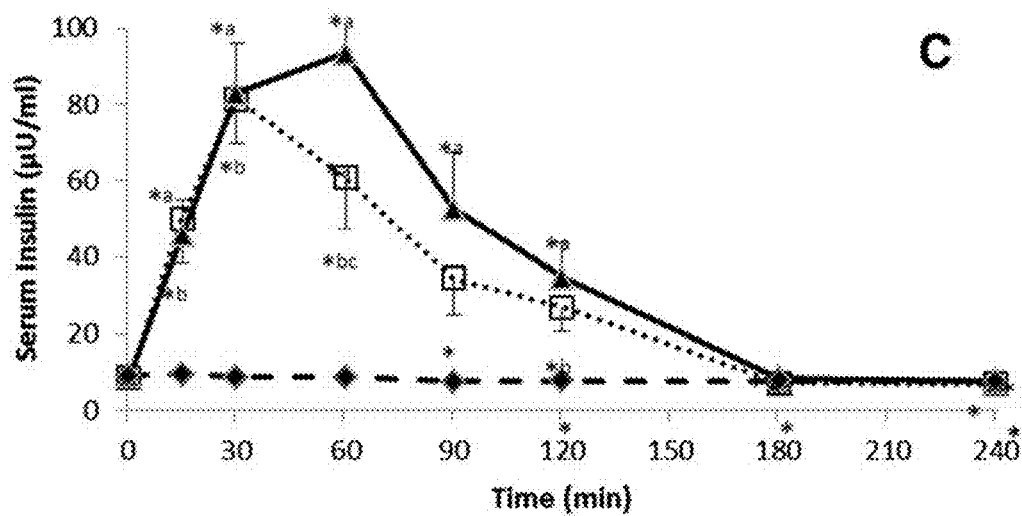

Ingestion of P alone did not alter postprandial insulin concentration. Insulin levels of the G+P treatment were significantly lower (P=0.002) than that of the glucose treatment at time 60 min (FIG. 1c). Repeated measures ANOVA found that serum insulin was significant according to time only (Table 2: Experiment 1). Insulin sensitivity obtained from oral glucose tolerance test and according to Caumo et al. formula increased following G+P treatment and the difference was close to significance (P=0.051) (Table 3: Experiment 1). While index of insulin sensitivity increased significantly (P=0.006) following the addition of P to OGTT (Table 3: Experiment 1). Insulin sensitivity of the P ingestion treatment was not determined since postprandial glucose and insulin levels were minimally affected.

TABLE 3

Measures of insulin sensitivity from oral glucose tolerance test

| Outcome variables | Placebo | Phosphorus | Paired t-test (P value) |
| --- | --- | --- | --- |
| Experiment 1 (n = 7) | | | |
| Insulin sensitivity index [30] | 5.69 ± 0.86 | 7.00 ± 1.06 | 0.006 |
| Insulin sensitivity [29] | 12.19 ± 3.85 | 20.22 ± 6.65 | 0.051 |
| Experiment 2 (n = 8) | | | |
| Insulin sensitivity index [30] | 9.17 ± 0.97 | 8.88 ± 0.78 | 0.633 |
| Insulin sensitivity [29] | 15.31 ± 2.58 | 18.39 ± 3.28 | 0.210 |

Figure 2A:
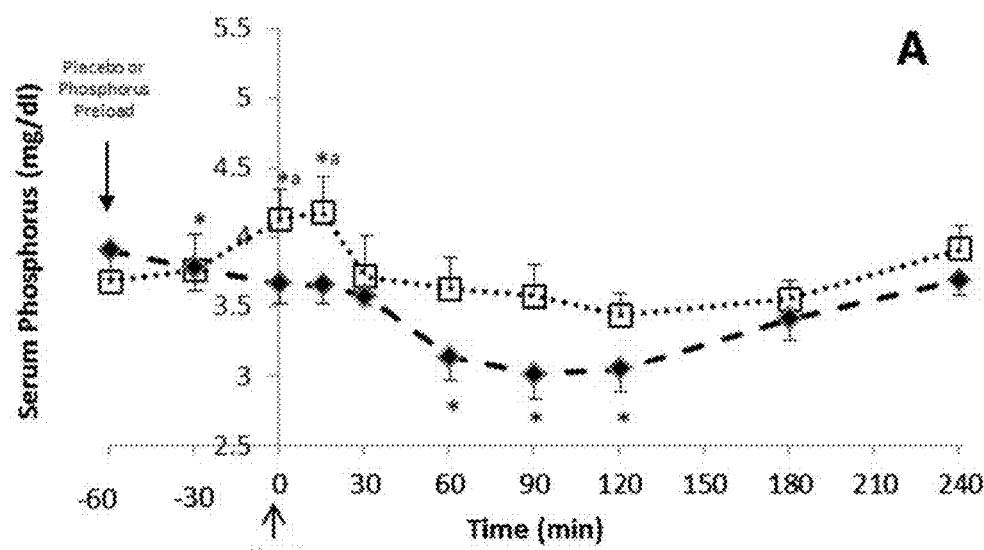
FIGS. 2A-2C are graphs showing the Changes in Serum Phosphorus (FIG. 2A), Glucose (FIG. 2B), and Insulin (FIG. 2C) levels of subjects in experiment 2. # Experiment 2: After the he ingestion of 75 g glucose 60 min after placebo (-♦-) or 500 mg phosphors (..□..) preload; * p-value<0.05: Paired t-test in the same treatment in comparison with baseline (time −60 min) value. A p-value<0.05: Paired t-Test between placebo and phosphorus preload treatments at each time point.
Figure 2B:
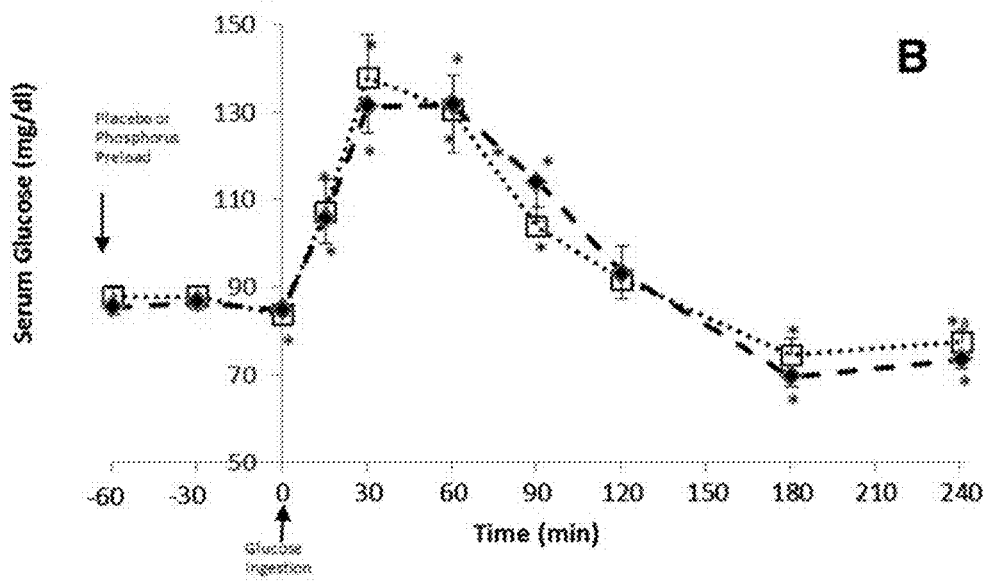

Ingestion of placebo tablets had no effect on serum P levels prior to glucose ingestion, but glucose ingestion decreased serum P levels (FIG. 2a). Following P ingestion, serum P levels increased significantly at time 0 and 15 min and then returned to baseline levels (FIG. 2a). Repeated measures ANOVA analysis of all time points showed that serum P was significant according to time and treatment (Table 2: Experiment 2). Serum glucose levels of the glucose and G+P treatments increased significantly following glucose ingestion (FIG. 2b). The increase in glucose levels was similar between the two treatments, except for a slight difference at time baseline and 240 min believed to be of no clinical significance (FIG. 2b). In line, repeated measures ANOVA were significant according to time only (Table 2: Experiment 2).

Figure 2C:
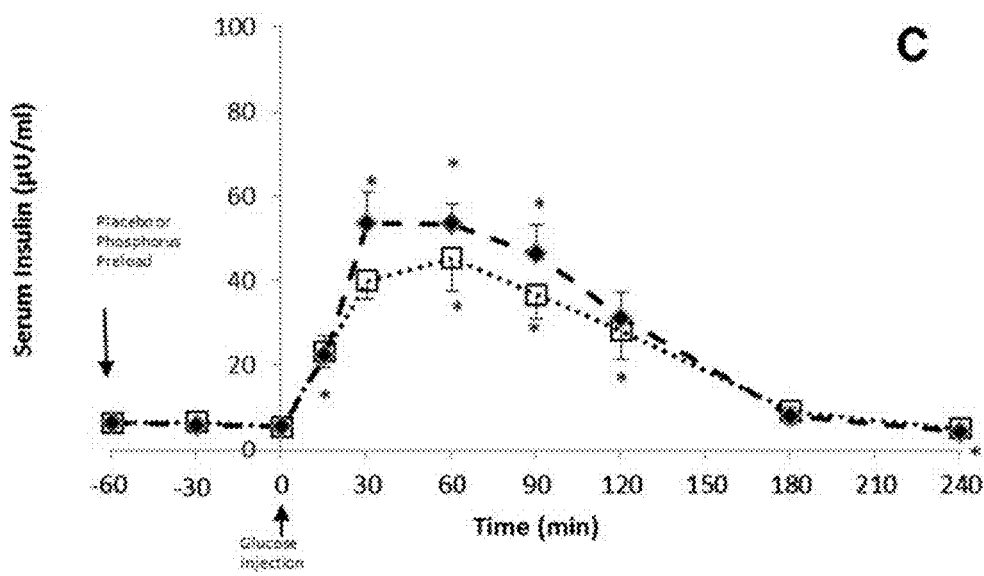

Glucose ingestion increased insulin levels of both treatments, but the magnitude of this increase was modestly lower in the P preload treated group (FIG. 2c) and repeated measures ANOVA failed to detect difference according to treatment (Table 2: Experiment 2). Measures of insulin sensitivity were found to be similar between the two treatments and this was expected since the changes in insulin and glucose were similar between the treatments (Table 2: Experiment 2).

Discussion

In agreement with other studies, ingestion of P alone (experiment 1 and 2) increased postprandial serum P, while ingestion of grape juice, glucose alone, or other type of carbohydrate reduced postprandial serum P levels. Glucose may indirectly affect P status through the stimulation of peripheral P uptake by insulin, which in turn stimulates the phosphorylation of several compounds including carbohydrate, fat and protein. About 60% of in-fused P has been reported to be translocated from the extracellular to the intracellular compartment, mainly in skeletal muscles. This translocation is believed to be mediated via insulin action as glucose infusion in pancreatectomic dogs failed to induce a reduction in serum P except when insulin became available. In line with this, the parallel increase in postprandial glucose and insulin (peaks at 30-60 min) was followed by a decrease in serum P (dip at 90 min). Therefore, under conditions of P intake alone, intracellular P is likely to have been affected since insulin was not altered.

In the current example, both co- and pre-ingestion of P were able to halt the drop in serum P levels following glucose ingestion. In the G+P treatment, increased P uptake and availability might have contributed to the drop in glucose and insulin levels at time 60 min, due to an increase in intracellular glucose trapping (phosphorylation), especially since insulin release depends on glucose circulation. This process might have played a role in the observed improvement in the measures of insulin sensitivity following P ingestion with glucose (Experiment 1). Phosphorylation or P trapping seems to have been substantially stimulated or became dependent on extracellular P 30 min after glucose ingestion; as indicated by the drop in postprandial serum P levels. This may partially be behind the failure of P preingestion to impact postprandial plasma glucose, since the majority of phosphorus is known to be absorbed within 60 min, as supported by the finding from experiment 1.

When glucose was ingested alone, the low availability of P may have hindered insulin phosphorylation capacity through creating competition for P. Such competition may have deleterious effects since it can affect glucose clearance and trapping, glycolysis and gluconeogenesis, and phospholipids and hepatic fat accumulation. Therefore, postprandial glycemia and insulinemia seem to be improved by exogenous P availability and this may partially explain the reported association between low serum P with insulin resistance and elevated blood glucose levels.

Ingestion of P before or with glucose was able to prevent the drop in postprandial serum P levels. The sustained high postprandial serum P in the G+P treatment in comparison to that of the glucose ingestion alone implies that intracellular P uptake may be controlled by a limited capacity for phosphorylation and/or glucose up-take. In healthy subjects, peripheral glucose uptake, especially in skeletal muscles, is known to be triggered by insulin dependent Glut 4 stimulation. While, intracellular glucose phosphorylation is controlled by the activities of glucokinase (liver) and hexokinase (muscle), the latter has a low Vmax (maximum velocity) capacity and is highly inhibited by glucose-P production. The reduction in serum glucose of the G+P treatment argues against a defect in Glut 4 (glucose uptake), therefore the sustenance in plasma P may have been attributed to the low Vmax capacity of muscle hexokinase. Accordingly, ingestion of higher P doses would not be expected to further improve glucose, insulin, or insulin sensitivity.

The fact that P is absorbed along the entire intestinal tract could be responsible for the observed high plasma P levels (above baseline value) in the G+P treatment beyond the time (120 min) of availability of glucose and insulin. Moreover, the difference in the magnitude of changes in postprandial glucose and insulin levels between the preload and the co-ingestion experiments implies that factors beyond the availability of circulating P, glucose and insulin may have been involved in improving of insulin sensitivity. The weak significant association seen between P preload on insulin sensitivity could be explained by the small sample size of the present example. On the other hand, glucose-phosphorus interaction in the proximal part of the small intestine may been involved in insulin sensitivity through incretin hormones. These hormones, especially glucagon like peptide-1 (GLP-1) and gastric inhibitory polypeptide (GIP) are known to be secreted in response to meal ingestion, especially high protein meals (rich in P) and were reported to affect insulin status and to play an important role in regulating postprandial blood glucose.

The observed improvement in the measures of insulin sensitivity following meal-phosphorus co-ingestion may have been partially involved in the reported synergic relationship between the intake of whole grains and glucose tolerance. Especially since this relationship was not explained by the function of dietary fiber and whole grains are rich in phosphors. Additionally, this observation may partially explain the observed parallel rise in metabolic syndrome with global urbanization and westernization of dietary habits, which favor low P intake. In comparison to other studies in the literature, which have used P injections to study its effect on glycaemia and insulinemia, the current example used a different method that mimicked daily dietary habits, through the ingestion of 500 mg of P with a glucose load (approximately 1.7 mg of P per Kcal). Therefore, these findings highlight the role of P in improving the states of hyperglycemia and hyperinsulinemia in healthy individuals without the influence of serum calcium and FGF-23 which did not vary when P is used.

On the other hand, elevated fasting serum P levels were reported to be associated with mortality among patients with chronic kidney and coronary diseases. The association was partially explained by the capacity of high P conditions to induce vascular calcification and endothelial injury using in vitro studies. Moreover, in a human (in vivo) study endothelial function impairment was apparent under high (1200 mg P/meal) and not normal (400 mg P/meal) P ingestion. In fact, the negligible impact of dietary P intake on serum P levels implies that factors associated with increased serum P, rather than P intake, were probably behind the association between cardiovascular disease and serum P. Recently, a weak association between dietary P intake and all-cause mortality was reported and this was questioned since participants adopted different dietary patterns and P intake was not the only variable. Thus, the nature of the relation between P intake and cardiovascular disease and mortality is far from clear and requires further scrutiny.

In the present example, sample size was based on the previously reported data of AUC for glucose. However, the observed large variations between subjects seem to have diluted the impact of the interventions. Further studies, using a larger sample size, would help in exploring the mechanisms by which the observed effects are mediated especially by examining the role of incretin hormones.

Although the dietary habits of these subjects were not assessed prior to the initiation of the study; however, as stated previously, fasting serum P status is not a good indicator of P intake. Postprandial status of the measured parameters is not likely to be affected by prior meal intake since all subjects were overnight fasted. Therefore, assessing dietary habits of subjects has no added implications on the example results.

Example 2: Increased Phosphorus Content of Preload Suppresses Ad Libitum Energy Intake at Subsequent Meal A preliminary set of experiments was conducted to investigate the effect of increased phosphorus content of a preload solution on subsequent food intake. The effect of water, sucrose (50 g), fructose (40 g fructose plus 10 g glucose) or glucose (50 g) preloads was examined with or without the addition of 500 mg of phosphorus (mixture of potassium and sodium phosphate). This work was approved by the Institutional Review Board of the American University of Beirut and written informed consent was obtained from all subjects. In brief, participants who had stable body weight for the last 3 months and were unrestrained eaters as assessed by the three-factor eating questionnaire were selected. All subjects were regular breakfast consumers and were asked to maintain their regular dietary and physical activity habits throughout the course of the example. Subjects were asked to avoid alcohol consumption, as well as any unusual strenuous exercise 24 h before the example. After a minimum of a 12-h fast, they consumed a standard breakfast (440 kcal) 4 h before presenting for the example. Participants chose a time between 1100 and 1400 to be convenient to perform the test; thereafter, they were asked to arrive at the same time on the same day of the week for the second study session. Thus, each experiment used a within-subject design, wherein each participant served as his or her own control.

In each experiment, two chilled preloads (with or without added phosphorus) were offered in a blind randomized order so as to control for the order-of-treatment effect. Each subject presented for two study days separated by a minimum of 1 week. All preloads were flavored with lemon to mask the taste of added phosphorus, had a volume of 250 ml and an additional 150 ml of pure water was offered to each subject (to wash out any after-taste); thus, a total of 400 ml of liquid solutions were drunk on each study day. At 80 min after the preload, an ad libitum lunch, consisting of standard pizza and water, was offered. Subjects were asked to eat freely until they felt 'comfortably full'; both food and water intakes were measured. Water intake was measured by weight (g) and food or energy intake (kcal) was obtained from the overall weight of pizza consumed.

In all experiments, the addition of phosphorus to the different preloads was associated with a significant reduction in energy intake at the subsequent meal (Table 4).

Table 4: Characteristics of subjects and ad libitum energy intake following the ingestion of phosphorus manipulated preloads.

TABLE 4

Characteristics of subjects and ad libitum energy intake following the ingestion of phosphorus manipulated preloads.

| Preload | Gender (n) | Age (years) | BMI (kg m−2) | Energy intake −P | (ad libitum) at subsequent meal +P |
|---|---|---|---|---|---|
| Water | M (12) | 23.8 ± 4.4 | 23.4 ± 3.0 | 1534 ± 341 | 1119 ± 210* |
| Sucrose | M (5), F (5) | 21.7 ± 4.0 | 2.2 ± 1.3 | 770 ± 379 | 532 ± 341* |
| Fructose | M (10), F | 6.6 ± 5.5 | 7.2 ± 1.4 | 1012 ± 407 | 676 ± 404* |
| Glucose | M (11) | 20.7 ± 1.4 | 24.7 ± 1.2 | 890 ± 308 | 652 ± 291** |

Abbreviations:
BMI, body mass index;
F, female;
M, male.
(−P): no added phosphorus to preload.
(+P): with 500 mg of added phosphorus to preload. Results are mean ± s.d.
*$P < 0.001$,
**$P < 0.01$, paired t-test (−P) vs (+P).

The magnitude of reduction varied slightly. The addition of phosphorus to the water preload led to 27% reduction in energy intake at the subsequent meal, similar to that of glucose (25%), while the addition of phosphorus to the sucrose or fructose preloads led to 33 and 35% reduction in energy intake at the subsequent meal, respectively. It is worth noting that phosphorus addition to the different preloads failed to affect water intake (data not shown), which indicates that the suppression of food intake was not due to osmotic differences caused by the presence or absence of phosphate. Data from the water preload experiment indicate that the reduction in subsequent energy intake is not dependent on carbohydrate energy content of the preload.

These findings are in support of the hypothesis that phosphorus content of a preload reduces subsequent food intake, although the exact mechanism by which this occurs was not investigated. What also remains to be studied is whether such an effect is influenced by body weight, and whether it persists in obese subjects.

The scope of the present study did not allow the scrutiny of central and/or peripheral factors. However, the present study provides human data wherein the stimulation of food intake and reduction in hepatic ATP status of rats after two 5 AM injections were reversed by pretreatment with a phosphorus infusion. Thus, it is prudent to assume that the negative association between phosphorus content of the preload and subsequent energy intake is related to hepatic ATP status, which is known to be attenuated by phosphate preloading. Such an assumption is in line with other human studies that have shown that hepatic ATP store and fractional recovery are inversely related to body mass index, and serum Pi is negatively related to body weight. Moreover, an analysis of metabolic data using the Knowledge Discovery in Databases procedure concluded that ATP deficiency or decreased energy levels were strongly linked to the development and sustenance of obesity, by driving overeating and conserving energy.

Hepatic ATP status is known to be influenced by both phosphorus content of a meal and hepatic phosphorylation of metabolites, and thus what still remains to be determined is whether phosphorus content of the second meal contributed to the observed reduction in energy intake. At the same time, it is not clear whether the effect of phosphorus content of preload on subsequent energy intake can be extended beyond the 80-min period used in this experiment. The present finding may in part help to clarify the existing controversy over the relationship between dairy product (high in phosphorus) consumption, calcium and body composition. In addition, these findings raise the possibility that the reduced energy intake observed in high-protein diets may partially be explained by the high phosphorus content of protein meals. These findings may also have implications for the consumption of refined cereal products, because cereals, particularly wheat, lose most of their phosphorus content during the refining process. This may call for the enrichment of refined cereals with phosphorus in an attempt to reduce energy intake.

Example 3: Increased Postprandial Energy Expenditure Following the Addition of Phosphorus to a High Carbohydrate Meal The objective was to determine the effect of phosphorus (P) ingestion with high carbohydrate meal on postprandial energy expenditure. P ingestion increases postprandial thermogenesis of the subjects.

A cross over study was conducted on six lean male subjects. Subjects received a 500 Kcal high carbohydrate meal (CHO: 65% E; Fat: 31% E; Protein: 4% E) with (500 mg of P) or without P. Energy expenditure was measured at baseline and at 30 minute intervals for 4 hours following meal ingestion using a ventilated hood and canopy system COSMED QUARK CPET unit.

Figure 3A:
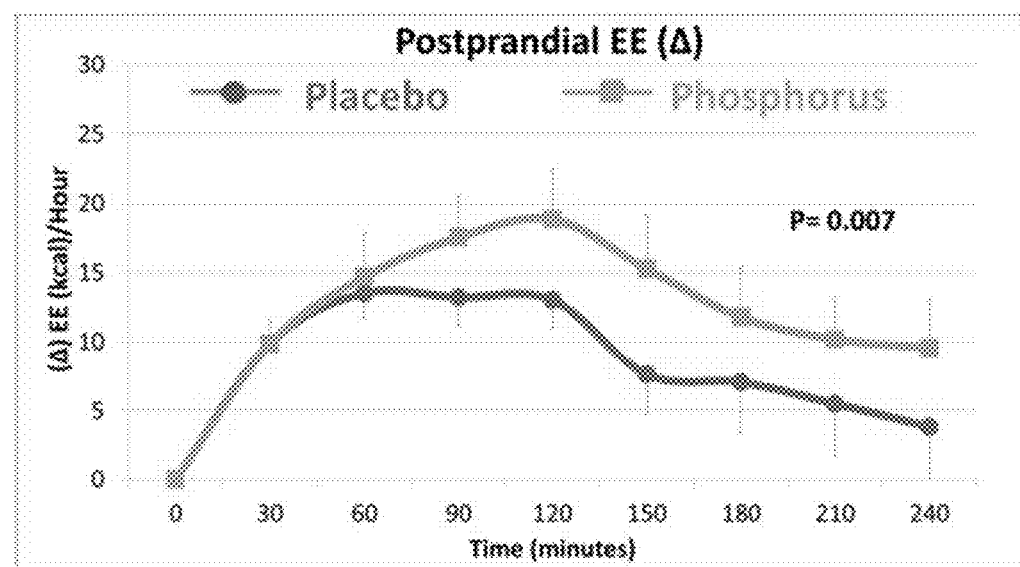
FIGS. 3A-3C are graphs shows the postprandial energy expenditure of meal containing P was significantly higher than that of placebo (p=0.007), this increase was associated with a significant rise in fat oxidation (%) (p=0.022, FIG. 3C), while carbohydrate oxidation (%) was decreased (p=0.023, FIG. 3B).
Figure 3B:
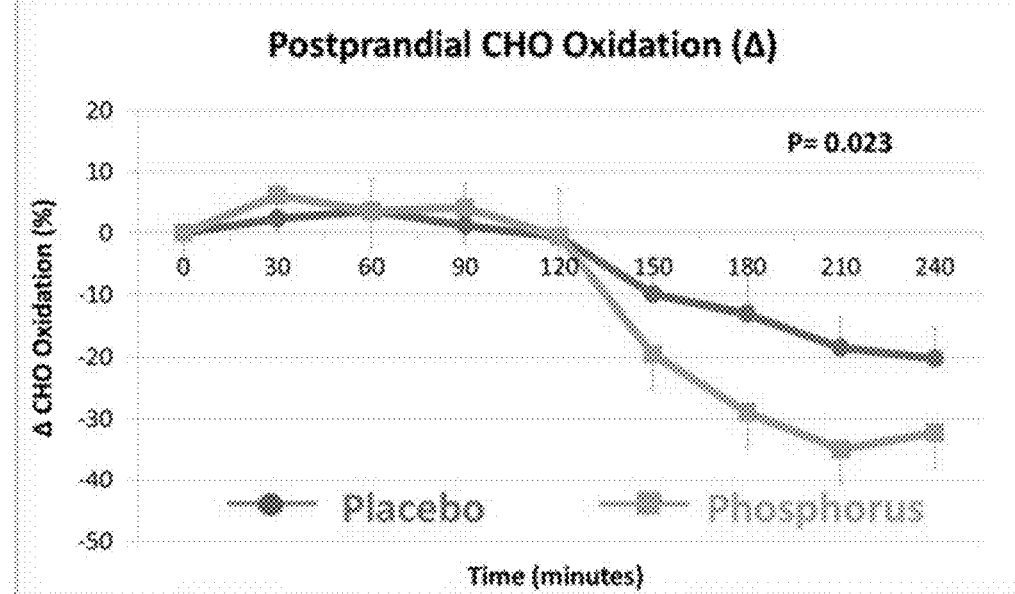
Figure 3C:
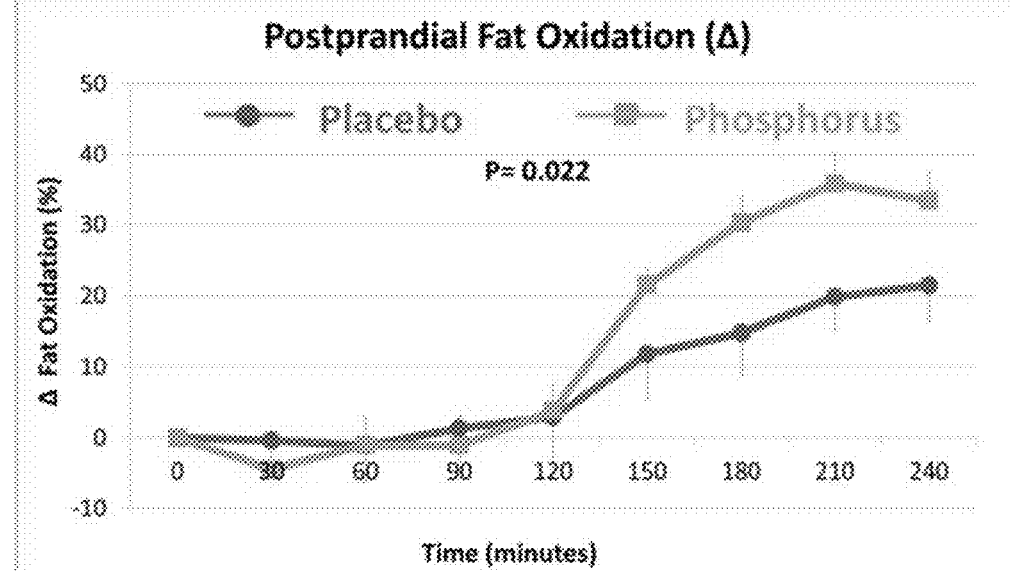

FIGS. 3A-3C shows the postprandial energy expenditure of meal containing P was significantly higher than that of placebo (p=0.007). This increase was associated with a significant rise in fat oxidation (%) (p=0.022), while carbohydrate oxidation (%) was decreased (p=0.023).

P was able to increase postprandial energy expenditure mainly due to increased fat oxidation. This data has promising effect for the management of obesity.

Figure 4:
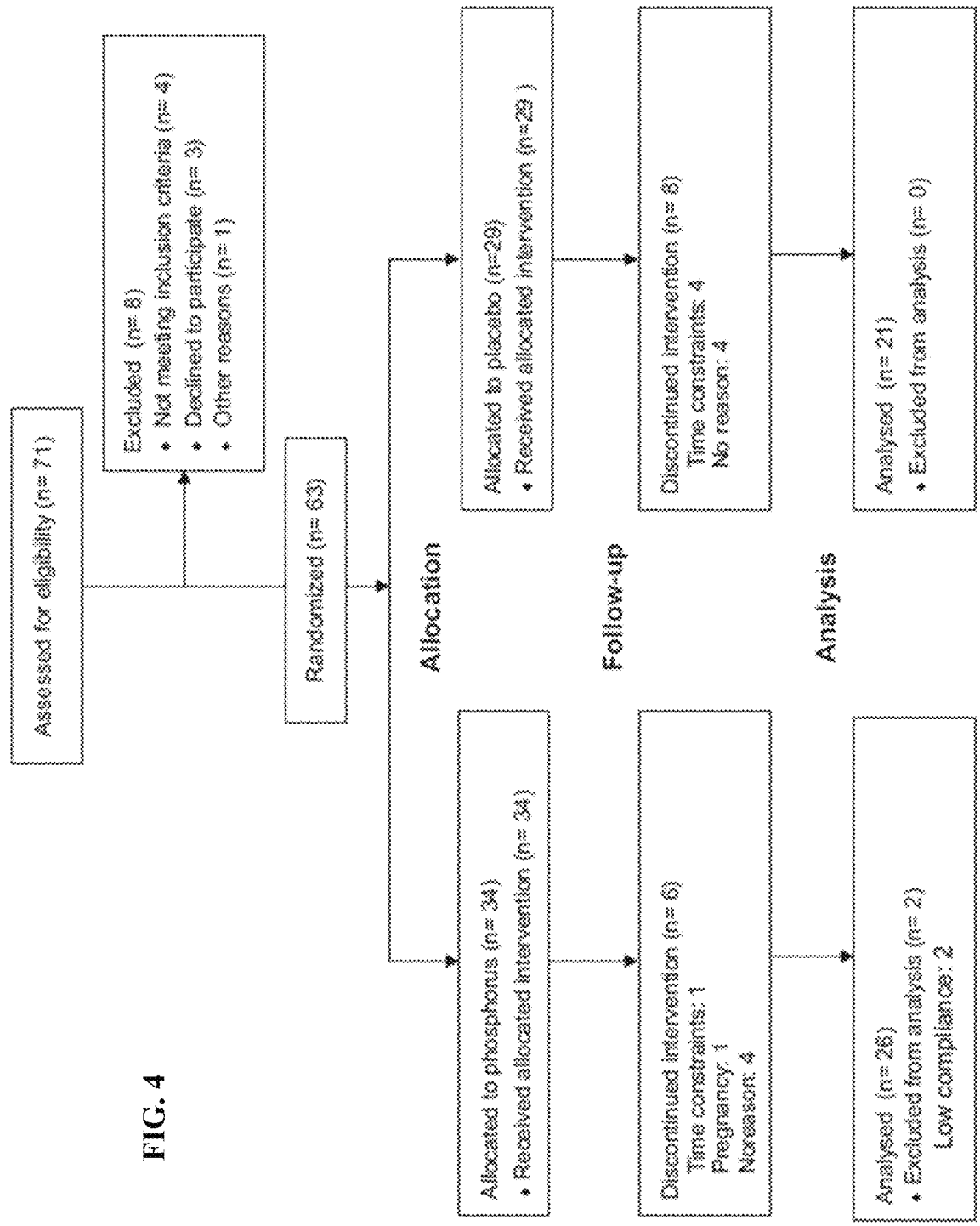
FIG. 4 is a Study flow diagram.

Example 4: Effect of Phosphorus Supplementation on Weight Gain and Waist Circumference of Overweight/Obese Adults Participants: After approval of the study by the institutional review board at the American University of Beirut (Beirut, Lebanon), 63 adults aged 18 to 45 years with a BMI ≥25 kgm−2, who provided signed informed consent, were recruited from the general public using poster advertisements or direct approach. Details about recruitment, randomization and follow-up are presented in FIG. 4. Exclusion criteria included glomerular filtration rate of 60 ml min−1 per 1.73 m$^2$, presence of any significant medical disease, pregnancy or lactation, regular administration of drugs that affect body weight and weight change of ≥3% within 3 months before the study. The enrollment of 40 subjects (20 per group) would detect a 10% change in weight of the placebo group, assuming the latter having a mean weight of 90 kg and s.d. of 10 kg, with 80% power and an α of 5%.

Randomization and Masking

This double-blind, randomized, controlled study allocated subjects into placebo group (n=21) or phosphorus group (n=26). Participants were requested to take three tablets containing either 375 mg phosphorus or a placebo (Nutricap Labs, Farmingdale, N.Y., USA) with each main meal (breakfast, lunch and dinner) for 12 weeks. They were asked to maintain regular dietary and physical activity habits during the entire study course and avoid alcohol consumption and any strenuous exercise 24 h before their visits (at baseline, 6 weeks and 12 weeks). Assignment to intervention or control group was made by having the principle investigator (corresponding author) ask the eligible subjects to blindly draw an envelope from a large box of 100 opaque, sealed envelopes (50 for each group), each containing a 2-cm by 2-cm paper with a written code designating intervention or control. There were no detectable differences in size or weight between intervention and control envelopes. In addition, both researchers and participants were blinded for the type of supplements that were similar in size, shape, color and odor.

Procedures

Subjects were asked to attend the research unit at baseline and after 6 and 12 weeks of participation. At baseline, anthropometric measurements and blood samples were collected and a subjective appetite questionnaire based on Wilson et al. Appetite assessment: simple appetite questionnaire predicts weight loss in community-dwelling adults and nursing home residents. AJCN 2005; 82:1074-1081 was completed. Participants were given a 6-week supply of the allocated supplement and were asked to attend the research unit at the end of this period. At 6 weeks, remaining tablets were collected and counted in order to assess adherence to the allocated intervention. Participants were then given a supply of the same type of supplementation for the consequent 6 weeks and were asked to complete the subjective appetite questionnaire. At 12 weeks, data were collected similar to the baseline visit, and remaining tablets were counted to assess compliance. Individuals who consumed 470% of the allocated tablets were excluded. Body weight and height (without shoes) were measured to the nearest 0.1 kg and 0.1 cm, using a calibrated Seca balance (Hamburg, Germany) and a portable stadiometer, respectively. Blood was withdrawn after overnight fast and samples were centrifuged for 15 min at 3500 r.p.m. at 3° C. for serum and plasma separation. Sample aliquots were stored at −80° C. until analysis. Serum phosphorus, creatinine, C-reactive protein, total cholesterol, high-density lipoprotein cholesterol, triglyceride and glucose levels were measured using the Vitros 350 analyzer (Ortho Clinical Diagnostics, Johnson and Johnson, Buckinghamshire, UK). The Friedwald formula was used to calculate low-density lipoprotein cholesterol levels. Friedewald W T, Levy R I, Fredrickson D S. Estimation of the concentration of low-density lipoprotein cholesterol in plasma, without use of the preparative ultracentrifuge. Clin Chem 1972; 18: 499-502. Fasting insulin concentration was measured using the ELISA kit (Diametra Millipore, Billerica, Mass., USA). HOMA-IR (homeostasis model assessment of insulin resistance) was calculated as described by Matthews et al. Homeostasis model assessment: insulin resistance and β-cell function from fasting plasma glucose and insulin concentrations in man. Diabetologia 1985; 28: 412-419. Glomerular filtration rate was calculated using CKD-EPI (Chronic Kidney Disease Epidemiology Collaboration) estimated glomerular filtration rate.

Statistical Analysis

Pairwise changes from baseline to 12-week follow-up anthropometric and biochemical variables were tested using paired t-tests, and intergroup assessment was performed using two-sample t-test. Repeated measures analysis of variance test was applied to analyze intragroup variation of appetite scores at different periods of time (baseline, 6 weeks and 12 weeks). Statistical analyses were conducted using SPSS 22 (Chicago, Ill., USA).

Abbreviations: BMI, body mass index; CRP, C-reactive protein; GFR, glomerular filtration rate; HDL-C, high-density lipoprotein cholesterol; HOMA-IR, homeostatic model assessment of insulin resistance; LDL-C, low-density lipoprotein cholesterol. SI conversion factor: to convert serum phosphorus to mmol 1-1, multiply by 0.323; cholesterol, LDL-C and HDL-C to mmol 1-1, multiply by 0.0259; triglycerides to mmol 1-1, multiply by 0.0113; glucose to mmol 1-1, multiply by 0.0555. Calculated as weight in kg divided by height in m squared. Measured at the midpoint between the lower rib and iliac crest. Because of missing data, based on sample size of 20 and 26 for placebo and phosphorus groups, respectively. Because of missing data, based on sample size of 20 and 25 for placebo and phosphorus groups, respectively.

Subject Characteristics

Baseline characteristics are shown in FIG. 5, and they were similar between groups. In all, 47 participants (placebo group n=21; phosphorus group n=26) completed the intervention, and all subjects had normal glomerular filtration rate (460 ml min−1 per 1.73 m$^2$) with a mean of 114.14 (10.19) ml min−1 per 1.73 m$^2$ and 112.24 (13.46) ml min−1 per 1.73 m$^2$ for the placebo and phosphorus groups, respectively. The mean age was 36.67 (9.76) years in the placebo group and 34.04 (11.24) years in the phosphorus group. No side effects were reported by participants over the experimental period.

Anthropometric Assessments

Changes in anthropometric and biochemical characteristics from baseline to 12 weeks are shown in FIG. 6. Body weight of the placebo group increased significantly from baseline by 1.13 kg (95% confidence interval (CI) 0.19 to 2.06), whereas that of the phosphorus group decreased by 0.65 kg (95% CI−1.69 to 0.40). These variations resulted in a significant difference (P=0.01) in the changes in body weight between the two groups. Consequently, the changes in BMI of the placebo group (0.42 kgm−2, 95% CI 0.05 to 0.78) was significantly different (P=0.01) than that of the phosphorus group (−0.24 kgm−2, 95% CI−0.59 to 0.12). Simultaneously, waist circumference of the phosphorus group was significantly reduced by 3.62 cm (95% CI−4.90 to −2.33), and this reduction was significantly different (Po0.001) from the small increase of 0.38 cm (95% CI−0.44 to 1.20) in the waist circumference of the placebo group.

Biochemical Assessments

Placebo or phosphorus treatment for 12 weeks did not affect serum levels of phosphorus, total cholesterol, low-density lipoprotein cholesterol, high-density lipoprotein cholesterol, tri-glyceride, glucose and C-reactive protein. Serum levels of insulin and HOMA-IR were similar between the two treatments at baseline and at 12 weeks, although a mild but significant difference was detected in their changes. This mild change is not believed to be of clinical significance (FIG. 6).

Subjective Appetite Scores

Baseline subjective appetite scores were similar between groups. The changes in several parameters of subjective appetite scores were found to decrease as the experiment progressed including that of appetite, quantity of food to reach fullness, hunger and number of snacks. However, changes in appetite, quantity of food to reach fullness, taste of food and number of snacks was significantly reduced in the phosphorus group as compared with the placebo as shown in FIG. 7.

Several dietary patterns and interventions were reported to improve body weight. High protein diets were constantly found to induce weight loss, probably because of their capacity to decrease energy intake and increase energy expenditure. Consumption of dairy products was also shown to be inversely related to body weight, whereby its increased intake among overweight individuals was reported to lower body weight, irrespective of its calcium content. Moreover, the intake of whole grains was shown to be negatively associated with the risk of different components of the metabolic syndrome, including body weight; however, the mechanism of such effect remains uncertain. This raises the questions on the role of macronutrients in weight reduction, especially as these dietary patterns or interventions have varied macronutrient profiles. The common feature between these diets seems to be their phosphorus content, as proteins, dairy products and whole grains are rich sources of phosphorus. This rationale for the involvement of low phosphorus status in the development of obesity and metabolic syndrome.

This study found that the ingestion of 375 mg phosphorus with each main meal, over a period of 12 weeks, was able to prevent weight gain and to reduce waist circumference among overweight and obese adults. However, minimal alterations were observed in the measured biochemical parameters (lipid profile, glucose and so on) that may be attributed to the modest baseline abnormalities in these parameters, short experimental duration and/or to the modest anthropometric changes. The absence of change in fasting plasma phosphorus further confirms that it is not a good marker of phosphorus intake.

The anthropometric changes in the phosphorus group are in line with other studies in which phosphorus status was reported to be inversely related to body weight and waist circumference. The mechanism(s) by which phosphorus affected body weight may have been related to its involvement in food intake control and/or energy metabolism. Phosphorus availability is known to stimulate ATP production, in particular hepatic ATP that is believed to transmit afferent neural signals to the central nervous system resulting in a decrease in food intake through the stimulation of satiation. Such effect was believed to be behind the impact of phosphorus addition to different carbohydrate preloads on the suppression of ad libitum energy intake at subsequent meal. In agreement, as reported in the subjective appetite questionnaires, satiation indicated by the quantity of food to reach fullness was reduced in the phosphorus group; however, the number of main meals, which is an indicator of satiety, was not reduced. Sustenance of hepatic ATP production over the postprandial and postabsorptive periods may have contributed to the observed reduction in appetite and number of snacks and these may have been translated by subjects into taste changes. Conversely, the similarity in the scores of hunger (that is, physiological controlled by depletion of energy stores) and the number of main meals between the phosphorus and placebo groups may be explained by a limited availability of hepatic ATP substrates beyond postprandial and postabsorptive periods, and thus an inability to impact the initiation of the next main meal. In brief, the impact of phosphorus supplement on energy intake seems to be related to its capacity to reduce the size of main meals (low appetite and high fullness) as well as intake between meals (number of snacks).

Furthermore, the favorable differences in body weight and waist circumference in the phosphorus group may have been partially related to an effect of phosphorus on energy metabolism. The addition of phosphorus to orange juice was reported to increase postprandial thermogenesis among obese but not lean subjects. In addition, phosphorus supplementation in a weight reducing program was found to increase resting metabolic rate of obese subjects. The pronounced reduction in waist circumference in the face of the modest reduction in body weight may have been attributed to changes in body composition. Weight gain under phosphorus-deficient diet was reported to be largely attributed to an increase in adipose tissue, whereas nitrogen retention was impaired, and this seems to mimic that of low-protein (low-phosphorus) diet. Changes in body fat were reported to be related to energy intake, whereas changes in lean body mass were related to the intake of protein, known to be high in phosphorus and this raises a question of whether the effect of protein on weight gain is linked to its content of phosphorus. It is not clear whether phosphorus supplementation favored lean body mass retention that ultimately masked the effect on changes in body weight because of its capacity to retain water. In any case, the observed reduction in waist circumference was similar to that reported in subjects under low-fat diets, and is believed to be of clinical significance as it is an indicator of abdominal obesity (visceral fat) that is known to be a risk factor of type 2 diabetes and cardiovascular disease.

Many concerns were raised on the relation between phosphorus status and cardiovascular disease and mortality, although the nature of the relation with phosphorus intake is far from clear and requires further scrutiny, especially as fasting serum phosphorus does not reflect intake as confirmed by the results. The fact that fasting but not non-fasting (that reflects intake rather than clearance) serum phosphorus levels were associated with increased mortality and fasting serum phosphorus level but not dietary intake were associated with coronary artery calcification may imply that factors behind or associated with elevated fasting serum phosphorus rather than phosphorus intake may have attributed to these detrimental effects. The recent reported weak association between dietary phosphorus intake and all-cause mortality was questioned as varied dietary habits or profiles were seen among the different dietary phosphorus intake quartiles. Moreover, such association may have been cofounded by the source of phosphorus in the diet, especially as dietary heme iron intake (derived from animal source that is also high in phosphorus) was shown to increase the risk of cardiovascular disease. It is believed that the need of phosphorus especially for carbohydrate metabolism may have been compromised by modernization (refinement and so on), particularly in staple carbohydrate-rich foods (rice, wheat and so on). The impact of such a compromise is expected to depend on the contribution of staple food to total energy intake and may partially be behind the drastic increase in obesity in developing countries, in particular as carbohydrate contribution to total energy intake is inversely related to income.

The strength of the study was that a rigorous system of training and certification of study personnel was developed and implemented for collecting all data. In addition, this study is pragmatic, randomized, double blinded and placebo controlled that required the use of tablets without requesting behavioral or dietary changes to avoid the problem of adherence.

Example 5: Effect of Macro-Mineral Supplementation on Sensory Properties and Postprandial Glycaemia of White Pita Bread Materials and Methods This study was conducted according to the guidelines laid down in the Declaration of Helsinki and all procedures involving human subjects/patients were approved by the Institutional Review Board (IRB) committee at the American University of Beirut (AUB). Written informed consent was obtained from all subjects. The clinical trial was registered with Clinical Trial.gov, NCT02598986. https://register.clinicaltrials.gov Wheat flour (80% extraction; Bakalian Flour Mills, Beirut, Lebanon) was used and levels of mineral supplementation were made. Restoration, whereby the level of added minerals to white flour aimed at attaining back original levels (prior to processing and milling), whereby each Kg of white flour contained 3.6 g $MgCO_3$ and 12.5 g $KH_2PO_4$. Fortification, whereby the level of added minerals to white flour was almost double that of original levels and each Kg of white flour contained 7.2 g $MgCO_3$ and 25 g $KH_2PO_4$. The amounts of added P and Mg are considered safe, since both are lower than the tolerable upper limits set at 4,000 mg/day and 350 mg/day for P and Mg, respectively. After supplementation, different types of pita bread were made and used for the different tests.

Pita Bread Making

Bread samples were prepared as previously in Toufeili I, Ismail B, Shadarevian S, et al. (1999) Role of Gluten Proteins in the Baking of Arabic Bread. *J Cereal Sci* 30 (3), 255-265. Dough contained flour (100 parts), sugar (2 parts), salt (1.6 parts), yeast (1 part) and water (57 parts). The ingredients were mixed (DITO SAMA, Model BM 20S, France) at low speed for 7 min until a smooth continuous dough was obtained. The dough was incubated at 40° C. for 15 min and the fermented dough was then divided into balls (~30 g) and proofed at 40° C. for 30 min. The balls were flattened into sheets, 1.5 mm thick, proofed at 40° C. for 15 min, and baked at 500° C. to optimum crust color. The bread loaves were placed in polyethylene bags and stored at −10° C.

Upon termination of the bread making process, the three bread types were then analysed for their mineral content by inductively coupled plasma mass spectrometry (ICP-MS) using the standard method EPA 200-7/8, (1991) Methods for the determination of metals in environmental samples.

Experiment 1: Difference and Acceptability Sensory Tests

Twenty four healthy untrained male volunteers participated in a difference/discrimination test. Two triangle tests (1 set of three samples at a time) were conducted to compare white pita bread (WP) vs. restored (WP-R) or vs fortified (WP-F) pita bread. Panelists were asked to indicate the odd sample in each set and to rinse their mouths before each sample. A consumer acceptability test was conducted with 60 healthy randomly recruited panelists (29 females and 31 males, mean age 22 years) from AUB as described in Lteif et al. The characterization of the physicochemical and sensory properties of full-fat, reduced-fat and low-fat ovine and bovine Halloumi Cheese. *J Dairy Sci* 92, 4135-4145 (2009). The three samples used in difference tests were assessed. Ten grams of each type of pita bread were prepared 2 hours prior to serving them and were stored in the refrigerator (4° C.). Panelists rated overall acceptability, appearance, colour, odour, flavour and texture on a 9-point hedonic scale. Lawless H T & Heymann H (2010) Sensory Evaluation of Food. Springer. All products were served in 59-mL plastic containers in individual booths. Panelists were instructed to rinse their mouths before each sample and the order of the samples within each set was randomized among the panelists in both tests.

Experiment 2: Determination of Postprandial Glycaemia

Twelve healthy males were randomly recruited and were asked to maintain their regular dietary and physical activity habits during the entire study course, and to avoid alcohol consumption as well as any unusual strenuous exercise 24 hours prior to each experimental session. A single blinded randomized, cross-over study was conducted. Participants were asked to complete a total of three experimental sessions, separated by a washout period of 10 days, and to consume one of the three different types of bread in random order. On each session, overnight fasted subjects were asked to ingest 90 g (containing 50 g of carbohydrate) of bread within 10-15 minutes (min) and subsequently drink 200 ml of water. Blood samples were collected at baseline (before bread ingestion) and at 15, 30, 45, 60, 90 and 120 min post bread ingestion. Blood samples were then centrifuged for 15 min at 4° C. at 1000 RPM and serum was stored in aliquots at −80° C. till analysis. Serum glucose, triglycerides (TG), total P, K and Mg were measured using the Vitros analyser 350 by Ortho-Clinical Diagnostics, Johnson & Johnson, New York.

Statistical Analysis

Experiment 1: Data related to triangle tests were analyzed by checking the minimum number of correct responses using a binomial table with p=0.05. Lawless H T & Heymann H (2010) Sensory Evaluation of Food, Springer. As for the acceptability test, a two-way analysis of variance using the GLM procedure of SAS® (version 9.02) was performed as described in Lteif et al. (2009). In the statistical model for acceptability, the response variable was the specific acceptability variable. Factors in the model were panelist and treatment (white, restored and fortified). Panelist was included as a random effect and treatment as a fixed effect. Means were separated by Tukey's honestly significant difference test. For all data, significance was established at $p<0.05$.

Experiment 2: GI, which is the incremental area under the 2-hour blood glucose response curve following a test food, compared to an equivalent carbohydrate amount of a control food (white bread) consumed by the same subject was calculated, as described in Wolever, T., Jenkins, D., Jenkins, A., et al. (1991) The glycemic index: methodology and clinical implications. Am J Clin Nutr 54 (5), 846-854. Area under the curve (AUC) and the GI rating (%) of the test foods WP-R and WP-F were calculated, as in Brouns, F., Bjorck, I., Frayn, K., et al. (2005) Glycaemic index methodology. Nutr Res Rev 18 (1), 145-171. Paired t-tests were used to compare differences between test foods (WP-R), (WP-F) and the control food (WP), at each time point. One-way ANOVA via Fisher's method was then used to detect statistical significance within the same bread type, at different time intervals. Repeated measures analysis of variance was used to determine statistical significance with effects for bread type, time, and bread type by time interaction.

Results

Pita bread analysis (Table 5) showed that WP-R bread's P, K and Mg contents were 84%, 60% and 200% higher than that of the WP, respectively. In the WP-F bread, P, K and Mg content were 260%, 230% and 410% higher than that of the WP bread, respectively. P, K and Mg contents of WP-F bread were almost double that of the WP-R bread.

TABLE 5

Phosphorus, potassium and magnesium content of the different pita bread type

| | Phosphorus (g/kg) | | Potassium (g/kg) | | Magnesium (g/kg) | |
|---|---|---|---|---|---|---|
| | Mean | SD | Mean | SD | Mean | SD |
| WP | 3.20 | 0.01 | 3.7 | 0.01 | 0.53 | 0.01 |
| WP-R | 5.90 | 0.00 | 5.9 | 0.23 | 1.60 | 0.04 |
| WP-F | 11.60 | 0.00 | 12.20 | 0.01 | 2.70 | 0.26 |

Results are expressed as the mean and standard deviation (SD).

Experiment 1

Difference Test and Hedonic Acceptability

In the triangle difference test, thirteen correct answers out of the 24 responses were needed to show a statistically significant difference. However, only 8 and 10 panelists responded correctly for the WP vs. WP-R ($p>0.05$) and WP vs. WP-F ($p>0.05$), respectively. Therefore, the triangle tests did not detect any significant differences between the different types of breads.

Moreover, the consumer acceptability test (Table 6) found no significant differences for most acceptability attributes (Overall Acceptability, Appearance, Colour, Odour and Flavour; $p>0.05$), except for texture ($p<0.05$) where the texture of WP was significantly more liked than the WP-F bread while no significant difference was detected between WP and WP-R breads or WP-R and WP-F breads.

TABLE 6

Hedonic acceptability variables for the different pita bread type

| Acceptability Variables | Overall Acceptability | | Appearance | | Colour | | Odour | | Flavour | | Texture | |
|---|---|---|---|---|---|---|---|---|---|---|---|---|
| | Mean | SD | Mean | SD | Mean | SD | Mean | SD | Mean | SD | Mean | SD |
| WP | 6.27 | 1.33 | 6.22 | 1.17 | 6.32 | 1.08 | 6.08 | 1.34 | 6.38 | 1.54 | $6.35^a$ | 1.72 |
| WP-R | 6.25 | 1.49 | 6.32 | 1.56 | 6.52 | 1.19 | 6.23 | 1.28 | 5.87 | 1.78 | $5.95^{ab}$ | 1.84 |
| WP-F | 6.07 | 1.33 | 6.28 | 1.21 | 6.40 | 1.39 | 6.12 | 1.53 | 5.85 | 1.62 | $5.42^b$ | 1.71 |
| Significance | 0.6010 | | 0.8609 | | 0.5422 | | 0.7945 | | 0.0657 | | 0.0042 | |

Results are expressed as mean and standard deviation (SD). $^{a,ab,b}$ Mean with unlike superscripts are different ($p<0.05$) as analyzed by paired t-test.

Experiment 2

Subjects Characteristics

Subjects' baseline characteristics are shown in Table 7. Subjects had a mean age of 24.5 years and were mainly normal and overweight subjects (mean BMI 26 kg/m$^2$). Baseline fasting levels of glucose, insulin, TG and total P indicate that subjects were all within normal ranges.

TABLE 7

Baseline characteristics of the 12 subjects

| | Mean | SEM |
|---|---|---|
| Age (yrs) | 24.50 | 1.02 |
| Weight (kg) | 83.92 | 3.35 |
| Height (m) | 1.79 | 0.01 |
| BMI (kg/m$^2$) | 26.03 | 0.67 |
| Fasting serum glucose (mg/dl) | 94.00 | 3.28 |
| Fasting serum insulin (μIU/mL) | 6.679 | 1.92 |
| Fasting serum triglycerides (mg/dl) | 91.47 | 3.78 |
| Fasting serum phosphate (mg/dl) | 3.79 | 0.19 |

Results are expressed as the mean and standard error of the mean (SEM).

Postprandial Mineral Responses

Figure 8A:
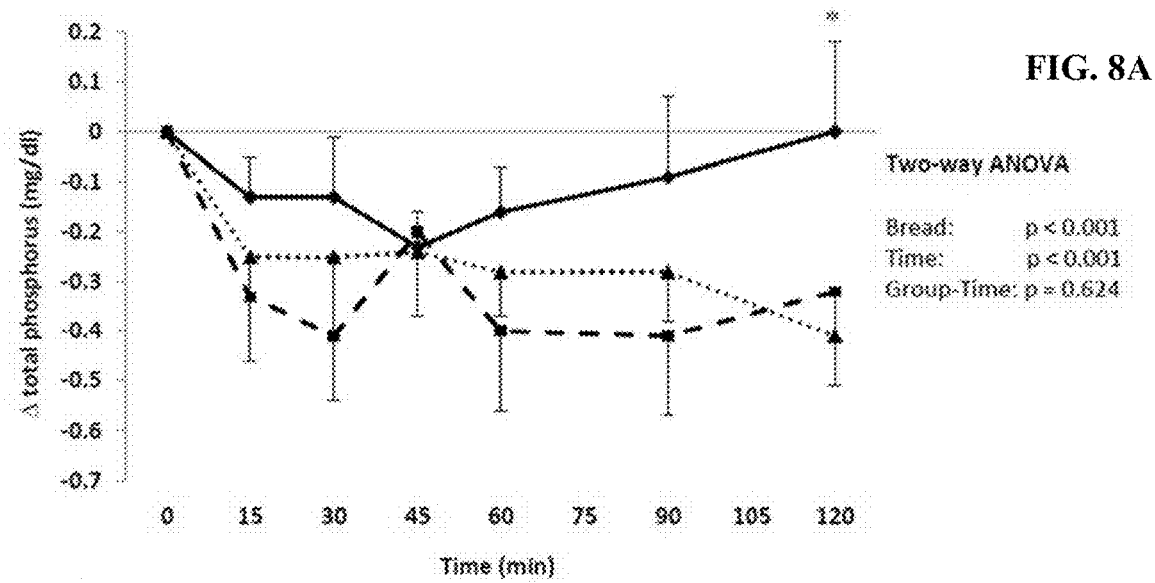
FIGS. 8A-8C are graphs showing the Postprandial changes (Δ) in the levels of total serum phosphorus (FIG. 8A), magnesium (FIG. 8B) and potassium (FIG. 8C) following the ingestion of the different types of pita breads [White pita bread: WP (- - ▲ - -); White pita bread-restored: WP-R (--■--); White pita bread fortified: WP-F (-♦-). * Values are significantly different from control test food (WP) within a specific time at p<0.05, as analyzed by paired t-test.

Ingestion of the different types of pita bread was found to alter postprandial level of the macro-minerals. Serum total P decreased following ingestion of all bread treatments and did not return to baseline level by the end of the experimental session, except for that of the WP-F. There was a significant difference between WP and WP-F treatments at 120 min. Additionally, changes in serum total P showed significant differences in serum total P between bread types ($p<0.001$) and across time intervals ($p<0.001$) (FIG. 8a).

Figure 8B:
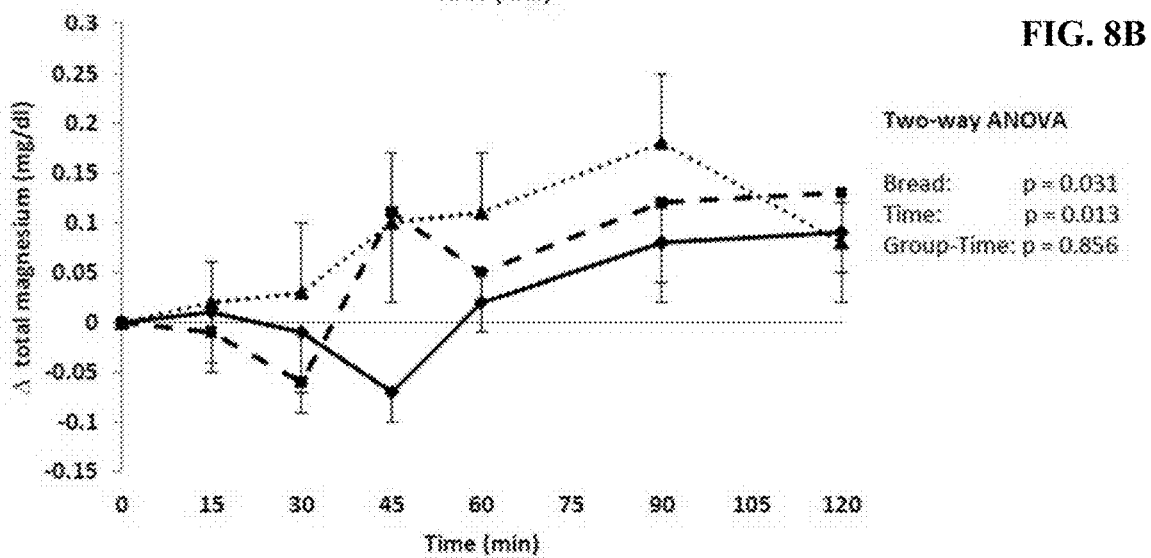

Postprandial serum Mg levels experienced a gradual increase following the ingestion of the different pita bread treatments. The increase seems to have been halted at 30 min in the WP-R and at 45 min in the WP-F treatments (FIG. 8b). There was a significant difference between WP and WP-F at 45 min. The changes in postprandial Mg were significant for bread types (p=0.031) and across time intervals (p=0.031). The magnitude of postprandial Mg increase seems to be inversely related to the Mg content of the bread.

Figure 8C:
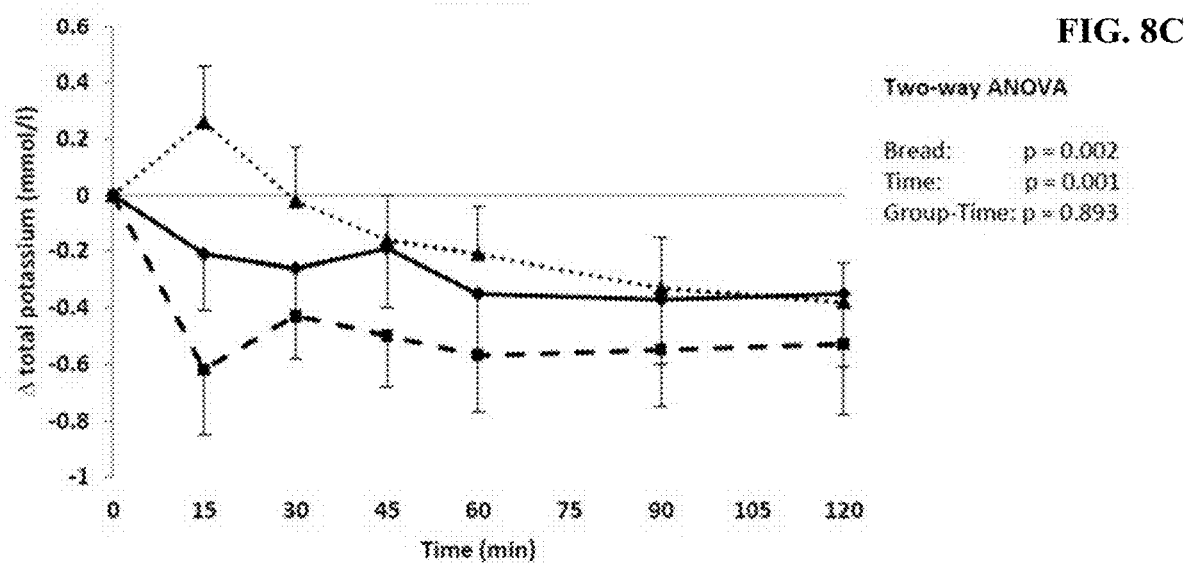

In contrast to that of Mg, changes in postprandial K levels experienced a decrease following the ingestion of the different bread treatments (FIG. 8c). Again, these changes were found to be significantly different for bread types (p=0.002) and across time intervals (p=0.001), whereby the magnitude of reduction seems to be more pronounced in the WP-R and WP-F treatments.

Postprandial Triglycerides and Glucose Responses

Figure 9A:
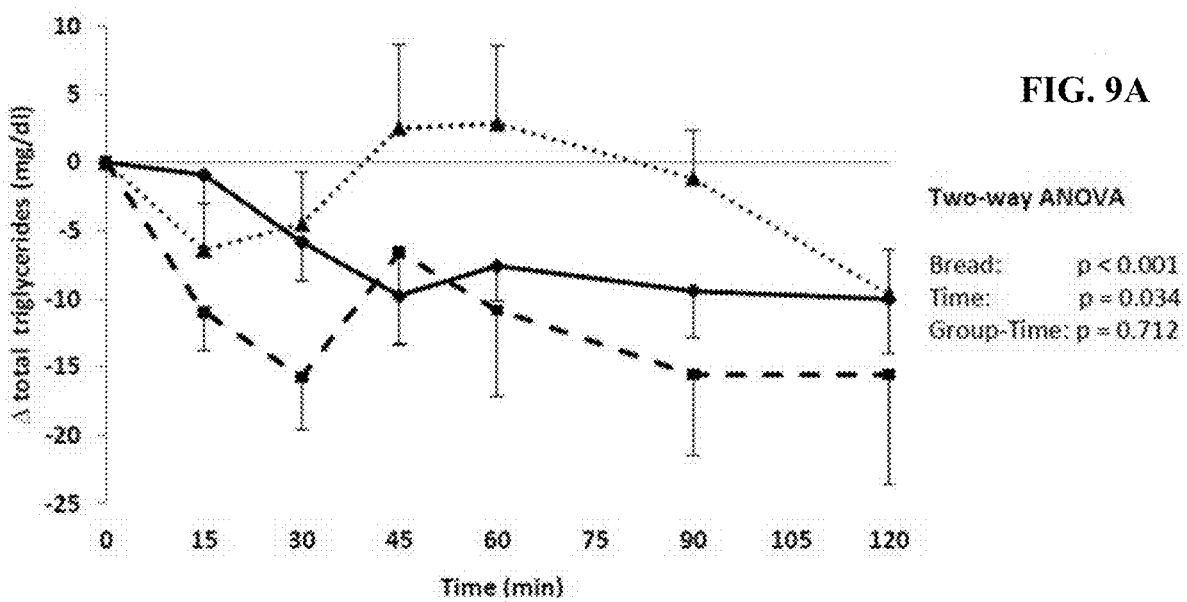
FIGS. 9A-9B are graphs showing the Postprandial changes (Δ) in the levels of serum triglycerides (FIG. 9A) and glucose (FIG. 9B) following the ingestion of the different types of pita breads. [White pita bread: WP (- - ▲ - -) White pita bread-restored: WP-R (--■--); White pita bread fortified: WP-F (-♦-)]; *, , * values are significantly different from control test food (WP) within a specific time at p<0.05, p<0.01, and p<0.001 respectively, as analyzed by paired t-test.

The pattern of changes in postprandial serum TG (FIG. 9a) was found to differ following the ingestion of the different types of breads. Changes in serum TG were significantly different for bread type (p<0.001) and time (p=0.034) (FIG. 9a), whereby WP-R and WF-R had lower levels of TG at several time points, though paired t-tests failed to detect any statistical significance for these time points (p>0.05).

Figure 9B:
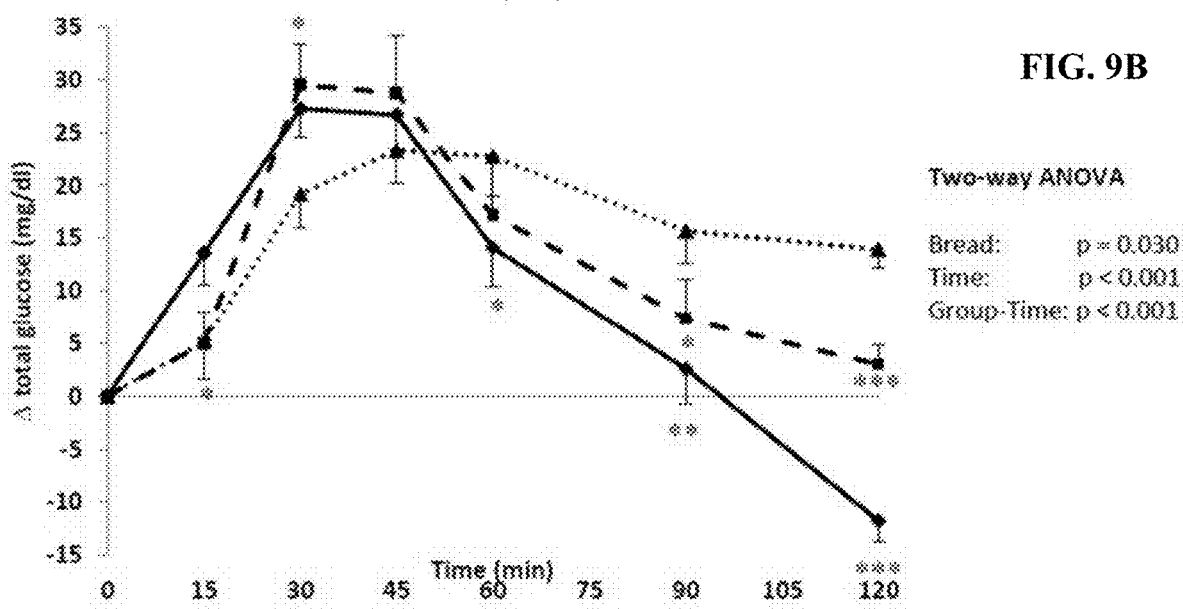
Figure 10:
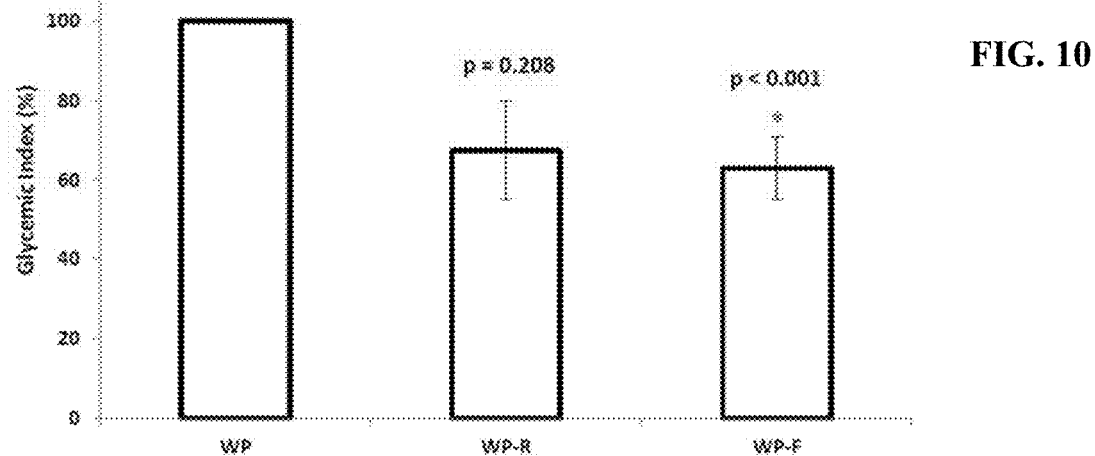
FIG. 10 is a graph showing the Glycemic index of supplemented pita breads as compared to white pita bread. WP: white pita bread; WP-R: white pita bread-restored; WP-F: white pita bread fortified. * Values are significantly different from white pita bread at p<0.05, as analyzed by paired t-test.

Postprandial serum glucose change (FIG. 9b) was found to vary between the different types of ingested breads. Analysis of variance revealed significant differences between bread types (p<0.030), time (p<0.001), and bread by time interaction (p<0.001). In brief, glucose levels peaked at 30-45 min post-ingestion. Thereafter, the rate of drop was faster in the supplemented bread types (WP-R and WP-F) compared to the control (WP). Paired t-tests showed significant differences between WP and WP-R at 30, 90, and 120 min; and between WP and WP-F at 15, 60, 90, and 120 min. At 60 min onwards, WP-R and WP-F significantly retained the lowest mean serum glucose change compared to WP. In line with the changes in postprandial glucose, the GI of WP-R and WP-F breads was 33% and 37% lower than that of the control bread (WP) (FIG. 10). The GI of WP-F (62.9±8.0; p<0.001) was significantly lower than that of control bread (WP), while that of the WP-R (67.3±12.5; p=0.208) failed to reach significance.

Discussion

The palatability of pita bread was not affected by the addition of macro-minerals as indicated by the lack of differences in the triangle and acceptability tests, although a small difference in texture was detected between WP and WP-F breads in the latter test. However, this difference was not detected by the panelists in the triangle tests, where subjects usually tend to be more attentive to differences and more analytical in their response. This possibly indicates that when the bread is assessed in its "entirety" the differences are not major. This is in line with others, where the addition of potassium, calcium and magnesium salts as replacements of NaCl did not yield any differences in appearance, texture and taste of brown bread. Thus, it can be concluded that the addition of macro-minerals to white wheat flour in an amount comparable to that found in whole wheat flour and even in quantities double that amount did not have any significant effect on the acceptability of pita bread.

The reduction in serum P following the ingestion of the different types of bread was in line with others. This drop is believed to be mediated by insulin that is known to stimulate glucose uptake into cells along with an intracellular shift of P to initiate glucose phosphorylation. The return of serum P to its baseline level at time 120 min in the WP-F type may have been related to its increased content of P while the failure of serum P in the WP-R to return to baseline level may imply that its content of P was not sufficient to fully meet the needs of intracellular phosphorylation.

On the other hand, the low postprandial levels of serum Mg in supplemented breads (WP-R and WP-F) as compared to that of WP may have been attributed to an enhanced clearance rate, especially since Mg clearance was reported to be dependent on insulin sensitivity that is known to be enhanced by P ingestion. Additionally, improved insulin sensitivity may have also contributed to the postprandial changes in serum K between supplemented (WP-R and WP-F) and WP breads. Furthermore, glucose clearance and insulin sensitivity were reported to be synergistically related to Mg and K statuses. Accordingly, the increased content of Mg and K in bread (WP-R and WP-F) may have further improved their own clearance rate.

In the macro-mineral supplemented breads, the reduction in postprandial glucose starting at 60 min may have been brought by the capacity of the added minerals to improve insulin sensitivity and thus glucose clearance. This suggests that glucose clearance and insulin sensitivity at 60 min after meal ingestion depend on exogenous factors including P, Mg and K.

Likewise, the ability of added minerals to improve insulin sensitivity may have been behind the observed reduction in serum TG of supplemented breads (WP-R and WP-F). Phosphorus status was reported to be correlated to a favourable lipid profile including increased HDL and decreased serum TG levels. Moreover, Mg supplementation was also shown to improve postprandial lipidaemic response in healthy subjects.

GI of supplemented breads relative to that of WP bread was reduced by 33 to 37% for WP-R and WP-F, respectively. The magnitude of reduction in GI was much higher than that observed in the micronutrient enriched steamed bread (about 25%), where glucose was used as a control. In summary, supplementation of white wheat flour with macro-minerals (P, Mg and K) did not affect the palatability of pita bread, while the GI was reduced. Consumption of about 500 g of WP-R, an excessive and high level outlier by any measure, would still be short of the upper limit for both P and Mg.

Worldwide, wheat and wheat products per capita daily consumption is about 180 g and this contributes to about 20% of total energy intake mainly in the form of bread and pasta. In Lebanon, bread intake, mainly in the form of white wheat pita bread, was reported to be about 146 g/d. The high palatability of white bread, a high GI food, made it very popular and a major contributor to the overall glycaemic load. Whole grain cereals that have low GI are known to have a protective role against the development of diabetes, abnormal lipid profile and obesity. However, the beneficial effect of whole wheat cereal products and specifically wheat bran was not identified in terms of the exact component that is behind these effects. This data indicates that the reduced GI of whole grain may be largely attributed to its content of macro-minerals, specifically potassium, K and Mg. It is worth noting that the ingestion of 200 g of WP-R (1200 mg of P) or WP-F (2320 mg of P) would still be below the upper limit of intake for P (4 g/d).

This example has successfully identified the potential beneficial role of minerals in improving the glycaemic response of white bread and overall glucose control in healthy male subjects. Even though the beneficial effects of whole grains have been widely publicized, the adoption of diets rich in whole grains still faces resistance. This might be due, at least in part, to the low palatability of unrefined cereal products. In this example, sensory results did not indicate any major effect of the experimental treatments on the quality of the bread, which is an encouraging outcome and indicative of the tolerance of bread quality to the addition of K and Mg. Results from the this example are promising and may beget future research that investigates the long term effect of mineral-supplemented bread on glycaemic status, and this may be used as a tool for the prevention or management of diabetes and other components of the metabolic syndrome All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of preventing weight gain and reducing waist circumference of a subject comprising delivering to the subject a composition comprised of at least between about 300 mg to about 500 mg of phosphorous in the form of a supplement or a food product; and
   the subject ingesting a meal comprising carbohydrate including a refined carbohydrate, an active concentration of potassium (K) at between 5.90 to 12.20 g/kg of the mass of the refined carbohydrate, and active concentration of magnesium (Mg) at between 1.60 to 2.70 g/kg of the mass of the refined carbohydrate; and an active concentration of phosphorous (P) in the refined carbohydrate;
   wherein the carbohydrate in the meal provides for about 300 to about 500 Kcal of the meal; and
   wherein the ingesting of the meal is about 30 to about 90 minutes after the delivering of the composition.

2. The method of claim 1, wherein the active concentration of phosphorus is between about 300 mg and about 500 mg per about 300 to about 500 Kcal of carbohydrate.

3. The method of claim 2, wherein the refined carbohydrate is a selected from the group consisting of flour, rice, sugars, cereals, and sweeteners.

4. The method of claim 3, wherein a source of phosphorus is selected from the group consisting of: phosphorus-based acids, monopotassium phosphate, phosphates, the phosphate ions, phospholipids, soluble salts of phosphate, bisphosphonate, a hydroxybisphosphonate, a phosphona e, a phosphate, and an aminomethylenephosphonic acid.

5. A method of reducing glycemic index of food provided to a subject comprising providing to the subject a macro mineral mixture comprising a ratio of phosphorous:potassium:magnesium of 1:1:0.3 by weight, wherein the macro mineral mixture is in the form of a supplement or food product; and the subject ingesting the macro mineral mixture and a food item comprising a refined carbohydrate, wherein the macro mineral mixture is at a ratio of about 10 mg of the mixture per gram of refined carbohydrate, which reduces the glycemic index of the refined carbohydrate by about 30%.

6. The method of claim 5, wherein the refined carbohydrate is selected from the group consisting of wheat, corn, rice, potato, sugar, and their byproducts.

7. The method of claim 6, wherein a source of phosphorus is selected from the group consisting of: phosphorus-based acids, monopotassium phosphate, phosphates, the phosphate ions, phospholipids, soluble salts of phosphate, bisphosphonate, a hydroxybisphosphonate, a phosphonate, a phosphate, and an aminomethylenephosphonic acid.

8. A method of increasing postprandial energy expenditure in a subject comprising providing to the subject a macro mineral mixture comprising a ratio of phosphorous:potassium:magnesium of 1:1:0.3 by weight, wherein the macro mineral mixture is in the form of a supplement or food product; and the subject ingesting the macro mineral mixture and a refined carbohydrate food item, wherein the macro mineral mixture is at a ratio of about 10 mg of the mixture per gram of refined carbohydrate, which increases the postprandial energy expenditure of the refined carbohydrate food item.

9. The method of claim 8, wherein the refined high carbohydrate food item is selected from the group consisting of wheat, corn, rice, potato, sugar, and their byproducts.

10. The method of claim 9, wherein a source of phosphorus is selected from the group consisting of: phosphorus-based acids, monopotassium phosphate, phosphates, the phosphate ions, phospholipids, soluble salts of phosphate, bisphosphonate, a hydroxybisphosphonate, a phosphonate, a phosphate, and an aminomethylenephosphonic acid.

* * * * *